(12) United States Patent
Blinkovsky et al.

(10) Patent No.: US 6,673,571 B2
(45) Date of Patent: Jan. 6, 2004

(54) POLYPEPTIDES HAVING AMINOPEPTIDASE ACTIVITY AND NUCLEIC ACIDS ENCODING SAME

(75) Inventors: Alexander Blinkovsky, Davis, CA (US); Tony S. Byun, Davis, CA (US); Alan V. Klotz, Dixon, CA (US); Alan Sloma, Davis, CA (US); Kimberly Brown, Elk Grove, CA (US); Maria Tang, Fairfield, CA (US); Mikio Fujii, Shizuoka (JP); Chigusa Marumoto, Shizuoka (JP); Lene Venke Kofod, Uggeløse (DK)

(73) Assignee: Novozymes Biotech, Inc., Davis, CA (US)

( * ) Notice: Subject to any disclaimer, the term of this patent is extended or adjusted under 35 U.S.C. 154(b) by 219 days.

(21) Appl. No.: 09/957,189

(22) Filed: Sep. 19, 2001

(65) Prior Publication Data

US 2002/0177210 A1 Nov. 28, 2002

Related U.S. Application Data

(60) Continuation of application No. 09/543,446, filed on Apr. 5, 2000, now Pat. No. 6,303,360, which is a division of application No. 09/192,104, filed on Nov. 13, 1998, now Pat. No. 6,184,020.
(60) Provisional application No. 60/069,719, filed on Dec. 16, 1997.

(51) Int. Cl.[7] ............................. C12P 21/06; C12N 9/00; C07H 21/04
(52) U.S. Cl. .................. 435/69.1; 435/183; 435/252.3; 435/252.31; 435/252.33; 435/320.1; 536/23.1; 536/23.2
(58) Field of Search .................. 530/300; 536/23.1, 536/23.2, 23.7, 23.74; 435/69.1, 183, 252.3, 252.33, 320.1, 252.31

(56) References Cited

U.S. PATENT DOCUMENTS 5,330,889 A 7/1994 Monget ........................ 435/34

FOREIGN PATENT DOCUMENTS

| EP | 733703 | 3/1996 |
| WO | WO 96/06175 | 2/1996 |
| WO | WO 96/28542 | 9/1996 |
| WO | WO 97/04108 | 2/1997 |

OTHER PUBLICATIONS

Nakada et al., 1972, Agricultural & Biological Chemistry 37: 757–765, 767–774, and 775–782.
Kwon et al., 1996, Journal of Industrial Microbiology 17: 30–35.
Gobbetti et al., 1995, Journal of Dairy Science 78: 44–54.
Telesnina et al., 1992, Antibiotiki I Khimioterapija 37: 14–16.
Chang and Smith 1989, Journal of Biological Chemistry 264: 6979–6983.
Chang et al., 1992, Journal of Biological Chemistry 267: 8007–8011.

*Primary Examiner*—Nashaat T. Nashed
(74) *Attorney, Agent, or Firm*—Robert L. Starnes

(57) ABSTRACT

The present invention relates to isolated polypeptides having aminopeptidase activity and isolated nucleic acid sequences encoding the polypeptides. The invention also relates to nucleic acid constructs, vectors, and host cells comprising the nucleic acid sequences as well as methods for producing and using the polypeptides.

7 Claims, 13 Drawing Sheets

```
ATCGGCCATGACCAGCAGTCAGTTCCACGTCGGCCTGCGGTTCGGCCGCCGATCACTTCGGCATCGATCTGG    70
TGAAACTGGCGATAGCGGCCCTTTTGCGGCGCTCATAGCGGAACAGGCCCCGTGCGTCGCGATCTTGA       140
GCGGGGCCGTGCTGCTGCCAGCCATTGGTGAGATAGGCCGGGCCGAGGCCCGGTGAATTCGGCCGCAG       210
CGTCAGCGATTCGCCGCCGGATCCTCGAACGAATACATTCCTTCGATACCACGTCGGTGGTTTCGCCC       280
AGCGAGCGGCGAGAACACCGTGGTCTTTTCGAAGACCCGGCATTTCCACCCGGCGAAAGCGATAGAGCTTGC   350
GCACGCGCTCGAACGTTTCCACGACATGGCCAAAGGCCTCGGCCTCAAGCCCGAAAATGTCCGGTGCC       420
ACGAATAGCCTTGGGTGTCGGAATGGTTTGCTTGCTCATGGCCGGGATAGCGGCTTTCGCGGTG            490
GGGGAAGCATCCGTGGCGATCCGCCGTATTGTGCCCCCAAGGCATTGGCCTGCCTTTCCGCCTTCCACGTCCACCTTG    560
CATGAAAGGCGCCATGCCCAAAACCCCCAAGGCATTGGCCTGCCTGCTTCCGCCCCTTTCCACGTCCACCTTG   630
                M   R   K   T   P   Q   G   I   G   L   L   S   A   L   S   T   S   T   L
GCACTTGCCACCCTGATCCTGGCGCTGCCCAGCTGGCAGCGGCGGAGCAACAGCGCCGA                 700
 A   L   T   L   I   L   A   Q   P   A   L   A   Q   V   Q   P   A   S   N   S   R   P
TGGCAGTGCCGATCGCTCATGGGGTGCCCGATGCGCAGGACGTGCCCCTATCCCGGCACGATCGGGCTGCA     770
 M   A   V   P   I   A   H   G   V   P   D   A   Q   D   V   P   Y   P   G   T   I   G   L   Q
GATCGATGCCACCGATCTGGCCACCGGCGCCCTGCGCTTCCGGGTGGTGGAAACCGTGCCGGTGGCCGATGCC    840
 I   D   A   T   D   L   A   T   G   A   F   R   V   V   E   T   V   P   V   A   A   D   A
AAGGAACTGATCCTGCAACTGCCTGCCAATGGGCCAGAAGCTGGCCTGAAGCATGGAGCATGGAATCGGCCTGCCGAGC   910
 K   E   L   I   L   Q   L   P   A   W   L   P   G   E   H   G   N   R   G   P   V   A   E
TGGCCGGCATCACGTTTGAAGCCAAGGGCCAGAAGCTGGCCTGGACCCGGGACCCGGTGAAGTGAACGC      980
 L   A   G   I   T   F   E   A   K   G   Q   K   L   A   W   T   R   D   P   V   E   V   N   A
```

Fig. 9A

```
GTTCCACATCCCCCTGCCCGCCGGCACCAGCGAAGTGGTGGCCCGCTTCATCCACACCTCGCCGCTGCGC  1050
 F  H  I  P  L  P  A  G  T  S  E  V  V  A  R  F  I  H  T  S  P  L  R
GACAGCGAAGGCCGCATCACCGTTACGCGCGAAATGCTCAACGTGCAGTGGGAGAAGATGAGCCTCTATC  1120
 D  S  E  G  R  I  T  V  T  R  E  M  L  N  V  Q  W  E  K  M  S  L  Y
CCGCCGGTCACTATGTGCGCCAGATCAAGGTGCGTCCCACCGTCAGTTTCCCGCAGGGCTGGACCGTGTT  1190
 P  A  G  H  Y  V  R  Q  I  K  V  R  P  T  V  S  F  P  Q  G  W  T  V  F
CACCCTGGATGGCAAGACGCAGAGCGGCGCAATACCGTGACCTGGGCCGAAACCGACTATGAA  1260
 T  A  L  D  G  K  T  Q  S  G  A  G  N  T  V  T  W  A  E  T  D  Y  E
ACCCTGGTCGATTCGCCGGATCTTTGCCGGGCTCTATGCCGGCATGATCTGGCCCACAACGTCTATT  1330
 T  L  V  D  S  P  I  F  A  G  L  Y  A  A  R  H  D  L  G  H  N  V  Y
TCGATCTGGTGGCCGACAAGCCCGAGCTGCTGGCCGATCAAGCCGGAAAACCTGGCCCTATCGAACCT  1400
 F  D  L  V  A  D  K  P  E  L  L  A  I  K  P  E  N  L  A  Y  R  N  L
GGCCGACGAAGCCGTGGGCGCATTCGGGGCGCCATTTCGATCACTACGATTTCCTGCTCGCGCTGACC  1470
 A  D  E  A  V  G  A  F  G  A  R  H  F  D  H  Y  D  F  L  L  A  L  T
GATCGCATGGGCAGCATCGGCCTGGAACACCACCGTTCCAGCGAAAACCAGCAGGAACCCAAGAGCCTGA  1540
 D  R  M  G  S  I  G  L  E  H  H  R  S  S  E  N  Q  Q  E  P  K  S  L
CCGACTGGGCCGCTATGACTGGGACCGCAACGTGATCGCCAATGATCAGCCCACAGCTGCCGGATGCAA  1610
 T  D  W  A  A  Y  D  W  D  R  N  V  I  A  H  E  F  S  H  S  W  D  G  K
GTATCGCCGCTCGGCCAAGCTGTGGACCCCAGACTATCGCCAGCCGATGCAGGACAACCTGCTGTGGGTC  1680
 Y  R  S  A  K  L  W  T  P  D  Y  R  Q  P  M  Q  D  N  L  L  W  V
TATGAAGGGCAGACGCAGTTCTGGGGCCTGGTGGCCGCTCGGGGCGTGCAGAGCAAGGACGTGG  1750
 Y  E  G  Q  T  Q  F  W  G  L  V  L  A  A  R  S  G  V  Q  S  K  D  V
TCTTGGGCAGCCTCGCAACTATGCCGGCACGTTCACCCAGACCGGGCGACTGGCGCTCGGTGGA  1820
 V  L  G  S  L  A  N  Y  A  G  T  F  T  Q  T  A  G  R  D  W  R  S  V  E
AGACAACGACGATGGATCCCAAGCCCTATTCTGCGCTTACCCGTAACGAG  1890
 D  T  T  M  D  P  I  F  A  A  R  K  P  K  P  Y  S  S  L  T  R  N  E
GACTATTACACCGAAGGCGGCGCTGGTGTGGCTGGAAGCGGACCAGATCATCCGCGATGGCACCGGCGGCA  1960
 D  Y  Y  T  E  G  A  L  V  W  L  E  A  D  Q  I  I  R  D  G  T  G  G
```

Fig. 9B

```
AGAAGGGCCTGATGATTTCGCCAAGGCGTTCTTTGGCGTGCGCGACGGCGATTGGGGCGTGCTGACCTA  2030
 K  K  G  L  D  D  F  A  K  A  F  F  G  V  R  D  G  D  W  G  V  L  T  Y

TGAATTCGATGACGTGGTCAAGACCCTCAACGGCGTCTATCCCTATGACTGGGCCACGTTCCTCAAGACC  2100
 E  F  D  D  V  K  T  L  N  G  V  Y  P  Y  D  W  A  T  F  L  K  T

CGCCTGCAGACGCCGGGCCAGCCCGTGCCGCTCGGGGGCATCGAGCGCGGCTACAAGCTGGAATTCA   2170
 R  L  Q  T  P  G  Q  P  V  P  L  G  G  I  E  R  G  Y  K  L  E  F

AGGACGAGCCCAACCCCTATGACAAGGCCCGCATGGCCGACGCCAAGGTGCTCAGCCTGTTCAACTCGCT  2240
 K  D  E  P  N  P  Y  D  K  A  R  M  A  D  A  K  V  L  S  L  F  N  S  L

GGGCGTGACGCTGGACAAGGACGGCAAAGTCACCGCCTCGCGCTGGGATGGCCCGGCGTTCAAGGCGGGG  2310
 G  V  T  L  D  K  D  G  K  V  T  A  S  R  W  D  G  P  A  F  K  A  G

CTGGTTTCGGGCATGCAGGTCGATGGCCGTGAACGGCGACGCCTATGACGCGGACAAGCTCAAGGGCGCGA  2380
 L  V  S  G  M  Q  V  M  A  V  N  G  D  A  Y  D  A  D  K  L  K  G  A

TCACCAATGCCAAGACCGGCAACCCGGGCGCCGGCCGCCCGATCGAACTGCTGGTCAAGCGTGACGATCG  2450
 I  T  N  A  K  T  G  N  P  G  A  G  R  P  I  E  L  L  V  K  R  D  D  R

CTTTGTCACGCTGCCGATCACCTATGCCGACGGCCTGCGCTGGCCGTGGCTGGTGCGCACGGCGCCGGGC  2520
 F  V  T  L  P  I  T  Y  A  D  G  L  R  W  P  W  L  V  R  T  A  P  G

ACGGCACCGACCGGCCTGGACAAGCTGCTGGCCCCGCACGCCAGCAAGCTGCCCGTGGGCAAGGCTGCCA  2590
 T  A  P  T  G  L  D  K  L  L  A  P  H  A  S  K  L  P  V  G  K  A  A

AGTGATGTGCAGGGCCCGGGCACCGGGCGGCCCAAGCCTGCATCTGGCGCTTCATCCCTGTTCCTG  2660
 K

GTGCTGCTGATGGCGGCACCGGGCGGCCTGTGTGCATCCCCTCACCCGCAACAGTGGCGAACTGG  2730

CCGATTCGCTGGCCATGGGCTTTGATTTTGCGGCGCTGGCATTCCTGTTGTCGCTGGTGCCACTGCTGCG  2800

CTGTGCCGATGCCGATACGATGCGGCAAAGCGCGGTGACAACGATGCCAACCGGCTGCTGGTGCTGTGC  2870
```

Fig. 9C

ATCACCACCGTTCTGACCGCAGTGGTGATGGCATCGATCGCCCGGCGAGCTGCCCCGCGGGCACATGGCG 2940

ATTCGCTGGCAAAGCTCCGGCTGATCGGGACGCTGGTGCTGACCTGGCTTTTGCCAACA 3000

Fig. 9D

SEQUENCE LISTING

<160> NUMBER OF SEQ ID NOS: 9

<210> SEQ ID NO 1
<211> LENGTH: 3000
<212> TYPE: DNA
<213> ORGANISM: Sphingomonas

<400> SEQUENCE: 1

```
atcggccatg accagcagtt ccacgtcggc ctgcggttcg gccgcgccga tcacttcggc      60
atcgatctgg tgaaactggc gatagcggcc cttttgcggg cgctcatagc ggaacagggc     120
cccgtgcgtc gcgatcttga gcggggcgtg ctgctgccag ccattggtga gataggcgcg     180
ggcgaggccg gcggtgaatt cgggccgcag cgtcagcgat tcgccgccgc gatcctcgaa     240
cgaatacatt tccttcgata ccacgtcggt ggtttcgccc agcgagcgcg agaacaccgt     300
ggtcttttcg aagaccggca ttccacccg gcgaaagcga tagagcttgc gcacgcgctc     360
gaacgtttcc acgacatggc caaaggcctc ggcctcaagc ccgaaaatgt cctgggtgcc     420
```

-continued

```
acgaatagcc ttgggtgtcg gaatggtttg cttgctcatg gcgcgcgcgg atagcggctt    480
tcgcgcggtg ggggaagcat ccgtggcgat ccgccgcgta ttgtgcccat ctggccgttg    540
cagatgagac cgcttggcgg catgaaaggc gccatgcgca aaaccccca aggcattggc     600
ctgctttccg cccttccac gtccaccttg gcacttgcca ccctgatcct ggcgcagccc    660
gcgctggcgc aggtgcagcc ggcgagcaac agccgcccga tggcagtgcc gatcgctcat    720
ggggtgcccg atgcgcagga cgtgccctat cccggcacga tcgggctgca gatcgatgcc    780
accgatctgg ccaccggggc gttccgggtg gtggaaaccg tgccggtggc ggccgatgcc    840
aaggaactga tcctgcaact gccggcctgg ctgccgggtg agcatggcaa tcgcggcccc    900
gtggccgagc tggccggcat cacgtttgaa gccaagggcc agaagctggc ctggacccgc    960
gacccggtgg aagtgaacgc gttccacatc cccctgcccg ccggcaccag cgaagtggtg   1020
gcccgcttca tccacacctc gccgctgcgc gacagcgaag gccgcatcac cgttacgcgc   1080
gaaatgctca acgtgcagtg ggagaagatg agcctctatc ccgccggtca ctatgtgcgg   1140
cagatcaagg tgcgtcccac cgtcagcttc ccgcagggct ggaccgtgtt caccgcgctg   1200
gatggcaaga cgcagagcgg cgcgggcaat accgtgacct gggccgaaac cgactatgaa   1260
accctggtcg attcgccgat ctttgccggg ctctatgccg cgcggcatga tctgggccac   1320
aacgtctatt tcgatctggt ggccgacaag cccgagctgc tggcgatcaa gccggaaaac   1380
ctggccgcct atcgcaacct ggccgacgaa gccgtgggcg cattcggcgc gcgccatttc   1440
gatcactacg atttcctgct cgcgctgacc gatcgcatgg gcagcatcgg cctggaacac   1500
caccgttcca gcgaaaacca gcaggaaccc aagagcctga ccgactgggc cgcctatgac   1560
tgggaccgca acgtgatcgc ccacgaattc agccacagct gggatggcaa gtatcgccgc   1620
tcggccaagc tgtggacgcc cgactatcgc cagccgatgc aggacaacct gctgtgggtc   1680
tatgaagggc agacgcagtt ctggggcctg gtcctggccg cacgctcggg cgtgcagagc   1740
aaggacgtgg tcttgggcag cctcgccaac tatgccggca cgttcaccca gaccgccggg   1800
cgcgactggc gctcggtgga agacacgacg atggatccca tcttcgccgc cgcaagccc    1860
aagccctatt cctcgcttac ccgtaacgag gactattaca ccgaaggcgc gctggtgtgg   1920
ctggaagcgg accagatcat ccgcgatggc accggcggca agaagggcct ggatgatttc   1980
gccaaggcgt tctttggcgt gcgcgacggc gattggggcg tgctgaccta tgaattcgat   2040
gacgtggtca agaccctcaa cggcgtctat ccctatgact gggccacgtt cctcaagacc   2100
cgcctgcaga cgccgggcca gccggtgccg ctcggcggga tcgagcgcgg cggctacaag   2160
ctggaattca aggacgagcc caaccccat gacaaggcgc gcatggccga tgccaaggtg    2220
ctcagcctgt tcaactcgct gggcgtgacg ctggacaagg acggcaaagt caccgcctcg   2280
cgctgggatg gccggcgtt caaggcgggg ctggtttcgg gcatgcaggt gatggccgtg    2340
aacggcgacg cctatgacgc ggacaagctc aagggcgcga tcaccaatgc caagaccggc   2400
aaccccggcg ccggccgccc gatcgaactg ctggtcaagc gtgacgatcg ctttgtcacg   2460
ctgccgatca cctatgccga tggcctgcgc tggccgtggc tggtgcgcac ggcgccgggc   2520
acggcaccga ccgggctgga caagctgctg gccccgcacg ccagcaagct gcccgtgggc   2580
aaggctgcca agtgatgtca ggggccgggc caagcctgca tctgggccgc ctggcccac    2640
cccgcttcat cctgttcctg gtgctgctga tgggcggcac cggggcgtgg tgggtgtggc   2700
atccctcac ccgcaacagt ggcgaactgg ccgattcgct ggccatgggc tttgattttg    2760
cggcgctggc attcctgttg tcgctggtgc cactgctgcg ctgtgccgat gccgatacga   2820
```

```
tgcggcaaag cgcggtggac aacgatgcca accgcgtgct ggtgctgtgc atcaccaccg    2880
ttctgaccgc agtggtgatg gcatcgatcg ccggcgagct gccccgcgcg gcacatggcg    2940
attcgctggc aaagctccgg ctgatcggga cgctggtgct gacctggctt tttgccaaca    3000
```

<210> SEQ ID NO 2
<211> LENGTH: 673
<212> TYPE: PRT
<213> ORGANISM: Sphingomonas

<400> SEQUENCE: 2

```
Met Arg Lys Thr Pro Gln Gly Ile Gly Leu Leu Ser Ala Leu Ser Thr
 1               5                  10                  15

Ser Thr Leu Ala Leu Ala Thr Leu Ile Leu Ala Gln Pro Ala Leu Ala
                20                  25                  30

Gln Val Gln Pro Ala Ser Asn Ser Arg Pro Met Ala Val Pro Ile Ala
            35                  40                  45

His Gly Val Pro Asp Ala Gln Asp Val Pro Tyr Pro Gly Thr Ile Gly
        50                  55                  60

Leu Gln Ile Asp Ala Thr Asp Leu Ala Thr Gly Ala Phe Arg Val Val
65                  70                  75                  80

Glu Thr Val Pro Val Ala Ala Asp Ala Lys Glu Leu Ile Leu Gln Leu
                85                  90                  95

Pro Ala Trp Leu Pro Gly Glu His Gly Asn Arg Gly Pro Val Ala Glu
            100                 105                 110

Leu Ala Gly Ile Thr Phe Glu Ala Lys Gly Gln Lys Leu Ala Trp Thr
        115                 120                 125

Arg Asp Pro Val Glu Val Asn Ala Phe His Ile Pro Leu Pro Ala Gly
    130                 135                 140

Thr Ser Glu Val Val Ala Arg Phe Ile His Thr Ser Pro Leu Arg Asp
145                 150                 155                 160

Ser Glu Gly Arg Ile Thr Val Thr Arg Glu Met Leu Asn Val Gln Trp
                165                 170                 175

Glu Lys Met Ser Leu Tyr Pro Ala Gly His Tyr Val Arg Gln Ile Lys
            180                 185                 190

Val Arg Pro Thr Val Ser Phe Pro Gln Gly Trp Thr Val Phe Thr Ala
        195                 200                 205

Leu Asp Gly Lys Thr Gln Ser Gly Ala Gly Asn Thr Val Thr Trp Ala
    210                 215                 220

Glu Thr Asp Tyr Glu Thr Leu Val Asp Ser Pro Ile Phe Ala Gly Leu
225                 230                 235                 240

Tyr Ala Ala Arg His Asp Leu Gly His Asn Val Tyr Phe Asp Leu Val
                245                 250                 255

Ala Asp Lys Pro Glu Leu Leu Ala Ile Lys Pro Glu Asn Leu Ala Ala
            260                 265                 270

Tyr Arg Asn Leu Ala Asp Glu Ala Val Gly Ala Phe Gly Ala Arg His
        275                 280                 285

Phe Asp His Tyr Asp Phe Leu Leu Ala Leu Thr Asp Arg Met Gly Ser
    290                 295                 300

Ile Gly Leu Glu His His Arg Ser Ser Glu Asn Gln Gln Glu Pro Lys
305                 310                 315                 320

Ser Leu Thr Asp Trp Ala Ala Tyr Asp Trp Asp Arg Asn Val Ile Ala
                325                 330                 335

His Glu Phe Ser His Ser Trp Asp Gly Lys Tyr Arg Arg Ser Ala Lys
            340                 345                 350
```

```
Leu Trp Thr Pro Asp Tyr Arg Gln Pro Met Gln Asp Asn Leu Leu Trp
            355                 360                 365

Val Tyr Glu Gly Gln Thr Gln Phe Trp Gly Leu Val Leu Ala Ala Arg
        370                 375                 380

Ser Gly Val Gln Ser Lys Asp Val Val Leu Gly Ser Leu Ala Asn Tyr
385                 390                 395                 400

Ala Gly Thr Phe Thr Gln Thr Ala Gly Arg Asp Trp Arg Ser Val Glu
                405                 410                 415

Asp Thr Thr Met Asp Pro Ile Phe Ala Ala Arg Lys Pro Lys Pro Tyr
                420                 425                 430

Ser Ser Leu Thr Arg Asn Glu Asp Tyr Tyr Thr Glu Gly Ala Leu Val
                435                 440                 445

Trp Leu Glu Ala Asp Gln Ile Ile Arg Asp Gly Thr Gly Gly Lys Lys
        450                 455                 460

Gly Leu Asp Asp Phe Ala Lys Ala Phe Phe Gly Val Arg Asp Gly Asp
465                 470                 475                 480

Trp Gly Val Leu Thr Tyr Glu Phe Asp Val Val Lys Thr Leu Asn
                485                 490                 495

Gly Val Tyr Pro Tyr Asp Trp Ala Thr Phe Leu Lys Thr Arg Leu Gln
                500                 505                 510

Thr Pro Gly Gln Pro Val Pro Leu Gly Gly Ile Glu Arg Gly Gly Tyr
            515                 520                 525

Lys Leu Glu Phe Lys Asp Glu Pro Asn Pro Tyr Asp Lys Ala Arg Met
            530                 535                 540

Ala Asp Ala Lys Val Leu Ser Leu Phe Asn Ser Leu Gly Val Thr Leu
545                 550                 555                 560

Asp Lys Asp Gly Lys Val Thr Ala Ser Arg Trp Asp Gly Pro Ala Phe
                565                 570                 575

Lys Ala Gly Leu Val Ser Gly Met Gln Val Met Ala Val Asn Gly Asp
                580                 585                 590

Ala Tyr Asp Ala Asp Lys Leu Lys Gly Ala Ile Thr Asn Ala Lys Thr
                595                 600                 605

Gly Asn Pro Gly Ala Gly Arg Pro Ile Glu Leu Leu Val Lys Arg Asp
        610                 615                 620

Asp Arg Phe Val Thr Leu Pro Ile Thr Tyr Ala Asp Gly Leu Arg Trp
625                 630                 635                 640

Pro Trp Leu Val Arg Thr Ala Pro Gly Thr Ala Pro Thr Gly Leu Asp
                645                 650                 655

Lys Leu Leu Ala Pro His Ala Ser Lys Leu Pro Val Gly Lys Ala Ala
                660                 665                 670

Lys

<210> SEQ ID NO 3
<211> LENGTH: 17
<212> TYPE: DNA
<213> ORGANISM: Sphingomonas
<220> FEATURE:
<221> NAME/KEY: misc_feature
<222> LOCATION: (1)...(17)
<223> OTHER INFORMATION: n = A,T,C or G

<400> SEQUENCE: 3
gcrtcrtang crtcncc                                                  17

<210> SEQ ID NO 4
<211> LENGTH: 17
```

-continued

```
<212> TYPE: DNA
<213> ORGANISM: Sphingomonas
<220> FEATURE:
<221> NAME/KEY: misc_feature
<222> LOCATION: (1)...(17)
<223> OTHER INFORMATION: n = A,T,C or G

<400> SEQUENCE: 4
aargaygarc cnaaycc                                                  17

<210> SEQ ID NO 5
<211> LENGTH: 17
<212> TYPE: DNA
<213> ORGANISM: Sphingomonas

<400> SEQUENCE: 5
acyttytcrt cyttrtc                                                  17

<210> SEQ ID NO 6
<211> LENGTH: 19
<212> TYPE: DNA
<213> ORGANISM: Sphingomonas

<400> SEQUENCE: 6
cttttcgtcc ttgtccagc                                                19

<210> SEQ ID NO 7
<211> LENGTH: 17
<212> TYPE: DNA
<213> ORGANISM: Sphingomonas

<400> SEQUENCE: 7
gcgtcatatg cgtctcc                                                  17

<210> SEQ ID NO 8
<211> LENGTH: 22
<212> TYPE: DNA
<213> ORGANISM: Sphingomonas

<400> SEQUENCE: 8
cgaatcggcc agatctccat cg                                            22

<210> SEQ ID NO 9
<211> LENGTH: 29
<212> TYPE: DNA
<213> ORGANISM: Sphingomonas

<400> SEQUENCE: 9
gatcctggcg cagctcgcga aggcgcagg                                     29
```

POLYPEPTIDES HAVING AMINOPEPTIDASE ACTIVITY AND NUCLEIC ACIDS ENCODING SAME

CROSS-REFERENCE TO RELATED APPLICATIONS

This application is a continuation of Ser. No. 09/543,446, filed on Apr. 5, 2000, now U.S. Pat. No. 6,303,360, which is a divisional of Ser. No. 09/192,104, filed on Nov. 13, 1998, now U.S. Pat. No. 6,184,020, which claims benefit of provisional application No. 60/069,719, filed on Dec. 16, 1997, and further claims priority of Danish application number 1465/97, filed on Dec. 16, 1997, and Danish application PA 1998 00670, filed on May 15, 1998, which applications are fully incorporated by reference.

BACKGROUND OF THE INVENTION

1. Field of the Invention

The present invention relates to isolated polypeptides having aminopeptidase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Various food products, e.g., soups, sauces and seasonings, contain flavoring agents obtained by hydrolysis of proteinaceous materials. This hydrolysis is conventionally accomplished using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Increasing concern over the use of flavoring agents obtained by chemical hydrolysis has led to the development of enzymatic hydrolysis processes.

Enzymatic hydrolysis of proteinaceous materials aims at obtaining a high degree of hydrolysis (DH), and this is usually attained using a complex of unspecific acting proteolytic enzymes (i.e., unspecific-acting endo- and exopeptidases). For example, WO 94/25580 describes a method for hydrolyzing proteins by use of an unspecific acting enzyme preparation obtained from *Aspergillus oryzae*. Specific acting proteolytic enzymes have not been used for this purpose because such enzymes only lead to an inadequate degree of hydrolysis.

Polypeptides having aminopeptidase activity catalyze the removal of one or more amino acid residues from the N-terminus of peptides, polypeptides, and proteins. Such polypeptides are classified under the Enzyme Classification Number E.C. 3.4.11.—of the International Union of Biochemistry and Molecular Biology.

WO 96/28542 discloses an aminopeptidase which has a moleculer weight of 35 kDa. JP-7-5034631 (Noda) discloses a leucine aminopeptidase obtained from yellow koji mold, which includes *Aspergillus oryzae* JP-7-4021798 (Zaidan Hojin Noda Sangyo) discloses the production of miso by adding a leucine aminopeptidase II prepared by cultivating a number of strains, including *Aspergillus oryzae* strain 460 (ATCC 20386) and strain IAM 2616. *Aspergillus oryzae* strain 460 is known to produce a number of leucine aminopeptidases of which three have a molecular weight of 26.5, 56, and 61 kDa by gel filtration (Nakada et al., 1972, *Agricultural and Biological Chemistry* 37: 757–765; Nakada et al., 1972, *Agricutural and Biological Chemistry* 37: 767–774; and Nakada et al., 1972, *Agricultural and Biological Chemistry* 37: 775–782; respectively). *Penicillium citrium* produces an intracellular leucine aminopeptidase with a molecular weight of 65 kDa by SDS-PAGE (Kwon et al., 1996, *Journal of Industrial Microbiology* 17: 30–35). *Lactobucillus helveticus* produces an endopeptidase of about 70 kDa which hydrolyzes peptides with 3–34 amino acid residues but not protein (EP 733,703). *Pseudomonas fluorescens* produces an intracellular aminopeptidase of about 50 kDa (Gobbetti et al., 1995, *Journal of Dairy Science* 78: 44–54). *Listeria monocytogenes* is reported to produce a glycine aminopeptidase (U.S. Pat. No. 5,330,889). WO 96/06175 discloses enzymes capable of degrading and detoxifying fumonisins. Telesnina et al., (1992, *Antibiotiki I Khimioterapiya* 37: 14–16) disclose the isolation of *Xanthomonas rebrilineans* protoplasts and their use in the study of aminopeptidase localization.

WO 97/04108 (Roehm) discloses DNA encoding an *Aspergillus sojae* leucine aminopeptidase. Chang and Smith (1989, *Journal of Biological Chemistry* 264: 6979–6983) disclose the molecular cloning and sequencing of a gene encoding a vacuolar aminopeptidase from *Saccharomyces cerevisiae*. Chang et al. (1992, *Journal of Biological Chemistry* 267: 8007–8011) disclose the molecular cloning and sequencing of a gene encoding a methionine aminopeptidase from *Saccharomycse cerevisiae*.

The production of protein hydrolysates with desirable organoleptic properties and high degrees of hydrolysis generally requires the use of a mixture of peptidase activities. It would be desirable to provide a single component peptidase enzyme which has activity useful for improving the organoleptic properties and degree of hydrolysis of protein hydrolysates used in food products either alone or in combination with other enzymes.

It is an object of the present invention to provide improved polypeptides having aminopeptidase activity and nucleic acid encoding the polypeptides.

SUMMARY OF THE INVENTION

The present invention relates to isolated polypeptides having aminopeptidase activity selected from the group consisting of:

(a) a polypeptide having an amino acid sequence which has at least 50% identity with amino acids 33 to 674 of SEQ ID NO:2;

(b) a polypeptide encoded by a nucleic acid sequence which hybridizes under low stringency conditions with (i) the nucleic acid sequence of SEQ ID NO:1 or (ii) its complementary strand; or a subsequence thereof of at least 100 nucleotides;

(c) an allelic variant of (a) or (b);

(d) a fragment of (a), (b), or (c), wherein the fragment has aminopeptidase activity; and (e) a polypeptide which (i) has aminopeptidase activity in the pH range between pH 5.0–8.5 measured at 37° C., (ii) has an isoelectric point in the range of 7.4–8.5; (iii) has aminopeptidase activity in the temperature range of 20–55° C., measured at pH 7.5 using Gly-pNA in Tris-HCl buffer; (iv) hydrolyzes Ala-pNA, Gly-pNA, Leu-pNA, Glu-pNA, Asp-pNA, Lys-pNA, Ile-pNA and Val-pNA; (v) does not hydrolyze Phe-pNA nor Pro-pNA; (vi) is not inhibited by phenylmethanesulfonyl fluoride, slightly inhibited by EDTA, di-isopropyl fluoro phosphate, p-chloromercuribenzoic acid and iodoacetic acid, completely inhibited by o-phenanthroline, and/or (vii) is obtained from a strain belonging to Sphingomonas and has a molecular mass of 67±5 kDa.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIGS. 9A–9D shows the nucleic acid sequence and the deduced amino acid sequence of a *Sphingomonas capsulata* IFO 12533 aminopeptidase (SEQ ID NOS:1 and 2, respectively).

DETAILED DESCRIPTION OF THE INVENTION

Polypeptides Having Aminopeptidase Activity

Figure 1:
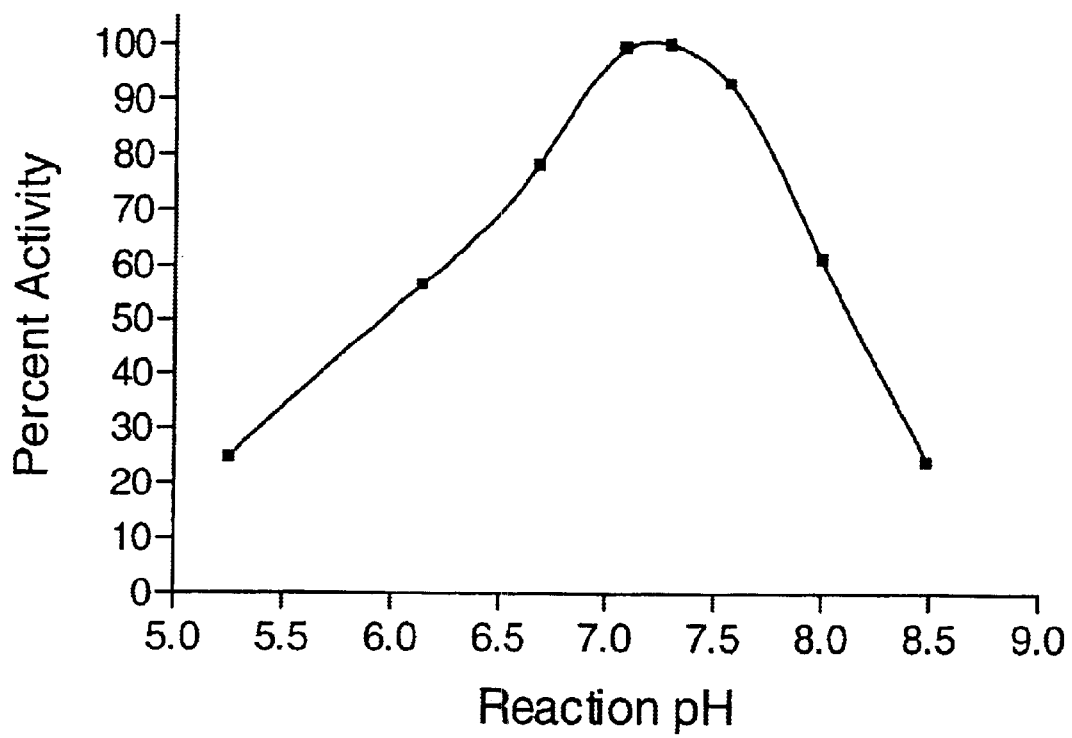
FIG. 1 shows the activity of a *Sphingomonas capsulata* aminopeptidase versus pH measured at room temperature using a 100 mg/ml solution of Ala-pNA in DMSO.

The term "aminopeptidase activity" is defined herein as a peptidase activity which catalyzes the removal of amino acids from the N-terminal end of peptides, oligopeptides or proteins. Defined in a general manner, the aminopeptidase activity is capable of cleaving the amino acid X from the N-terminus of a peptide, polypeptide, or protein, wherein X may represent any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val, but at least Ala, Gly, Leu, Glu, Asp, Lys, Ile and/or Val. It will be understood that the isolated polypeptides having aminopeptidase activity of the present invention may be unspecific as to the amino acid sequence of the peptide, polypeptide, or protein to be cleaved. For purposes of the present invention, aminopeptidase activity is determined by measuring the initial rate of hydrolysis of the p-nitroanilide of alanine at 405 nm.

In a first embodiment, the present invention relates to isolated polypeptides having an amino acid sequence which has a degree of identity to amino acids 33 to 674 of SEQ ID NO:2 (i.e., the mature polypeptide) of at least about 50%, preferably at least about 55%, preferably at least about 60%, preferably at least about 65%, preferably at least about 70%, more preferably at least about 80%, even more preferably at least about 90%, most preferably at least about 95%, and even most preferably at least about 97%, which have aminopeptidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two or more amino acid sequences is determined by the BLAST 2.0 protein database search program (Altschul et al., 1997, *Nucleic Acids Research* 25: 3389–3402) with the following arguments: blastall-p blastp-a 4-e 10-E 0-v 500-b 250-I [query file]-d prot_all, where -p refers to the program name, -a refers to the number of processors to use, -e refers to the expectation value, -E refers to the cost to extend a gap, -v refers to number of one-line descriptions, -b refers to the number of alignments to show, -I refers to the query file, and -d refers to the database used for the search.

Preferably, the polypeptides of the present invention comprise the amino acid sequence of SEQ ID NO:2 or an allelic variant thereof; or a fragment thereof, wherein the fragment has aminopeptidase activity. In a more preferred embodiment, the polypeptides of the present invention comprise the amino acid sequence of SEQ ID NO:2. In another preferred embodiment, the polypeptide of the present invention comprises amino acids 33 to 674 of SEQ ID NO:2, which is the mature polypeptide of SEQ ID NO:2, or an allelic variant thereof; or a fragment thereof, wherein the fragment has aminopeptidase activity. In another preferred embodiment, the polypeptide of the present invention comprises amino acids 33 to 674 of SEQ ID NO:2. In another preferred embodiment, the polypeptide of the present invention consists of the amino acid sequence of SEQ ID NO:2 or an allelic variant thereof; or a fragment thereof, wherein the fragment has aminopeptidase activity. In another preferred embodiment, the polypeptide of the present invention consists of the amino acid sequence of SEQ ID NO:2. In another preferred embodiment, the polypeptide consists of amino acids 33 to 674 of SEQ ID NO:2 or an allelic variant thereof; or a fragment thereof, wherein the fragment has aminopeptidase activity. In another preferred embodiment, the polypeptide consists of amino acids 38 to 654 of SEQ ID NO:2.

A fragment of SEQ ID NO:2 is a polypeptide having one or more amino acids deleted from the amino and/or carboxyl terminus of this amino acid sequence. Preferably, a fragment contains at least 524 amino acid residues, more preferably at least 574 amino acid residues, and most preferably at least 624 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the homologous polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a second embodiment, the present invention relates to isolated polypeptides having aminopeptidase activity which are encoded by nucleic acid sequences which hybridize under low stringency conditions, more preferably medium stringency conditions, even more preferably high stringency conditions, and most preferably very high stringency conditions, with a nucleic acid probe which hybridizes under the same conditions with the nucleic acid sequence of SEQ ID NO:1 or its complementary strand; or a subsequence thereof which encodes a polypeptide fragment which has aminopeptidase activity (J. Sambrook, E. F. Fritsch, and T. Maniatus, 1989, *Molecular Cloning, A Laboratory Manual*, 2d edition, Cold Spring Harbor, N.Y.); or allelic variants and fragments of the polypeptides, wherein the fragments have aminopeptidase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having aminopeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having aminopeptidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, the carrier material is used in a Southern blot. For purposes of the present invention, hybridization indicates that the nucleic acid sequence hybridizes to a nucleic acid probe corresponding to the nucleic acid sequence shown in SEQ ID NO:1, its complementary strand, or a subsequence thereof, under low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is nucleotides 670 to 2592 of SEQ ID NO:1, which encodes a mature polypeptide having aminopeptidase activity. In another preferred embodiment, the nucleic acid probe is the nucleic acid sequence contained in plasmid pMRT004.1-14 which is contained in *Escherichia coli* NRRL B-30032, wherein the nucleic acid sequence encodes the polypeptide of SEQ ID NO:2. In another preferred embodiment, the nucleic acid probe is the nucleic acid sequence encoding the mature polypeptide of SEQ ID NO:2 (i.e., amino acids 33 to 674) contained in plasmid pMRT004.1-14 which is contained in *Escherichia coli* NRRL NRRL B-30032.

For long probes of at least 100 nucleotides in length, low to very high stringency conditions are defined as prehybridization and hybridization at 42° C. in 5×SSPE, 0.3% SDS, 200 μg/ml sheared and denatured salmon sperm DNA, and either 25, 35 or 50% formamide for low, medium, and high and very high stringencies, respectively, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to isolated polypeptides having the following physicochemical properties: (a) aminopeptidase activity in the pH range between pH 5.0–8.5 measured at 37° C., (b) an isoelectric point (pI) in the range of 7.4–8.5; (c) aminopeptidase activity in the temperature range of 20–55° C., measured at pH 7.5 using Gly-pNA in Tris-HCl buffer; (d) hydrolyzes Ala-pNA, Gly-pNA, Leu-pNA, Glu-pNA, Asp-pNA, Lys-pNA, Ile-pNA and Val-pNA; (e) does not hydrolyze Phe-pNA nor Pro-pNA; (f) is not inhibited by phenylmethanesulfonyl fluoride, slightly inhibited by EDTA, di-isopropyl fluoro phosphate, p-chloromercuribenzoic acid, and iodoacetic acid, completely inhibited by o-phenanthroline, and/or (g) is obtained from a strain belonging to Sphingomonas and has a molecular mass of 67±5 kDa.

In a preferred embodiment, the polypeptide has aminopeptidase activity in the pH range between pH 5.0–8.5 measured at 37° C., more preferably in the pH range 6.5–8.0, and even more preferably having the highest aminopeptidase activity in the pH range 7.0–7.5 measured at 37° C.

The isoelectric point of the aminopeptidase is variable since the isoelectric point of the freshly prepared enzyme is estimated as 8.4 using an activity staining method, however, the isoelectric point varies from 7.4 to 8.5 during the course of purification and/or storage. The uncertainty of the isoelectric point may be due to the self digestion of the aminopeptidase from its amino terminal.

In another preferred embodiment, the polypeptide has a molecular mass of 67±5 kDa, more preferably a molecular mass of 67±2 kDa and is obtained from a strain belonging to Sphingomonas, more preferably *Sphingomonas capsulata* and most preferably *Sphingomonas capsulata* IFO 12533. The molecular mass is measured by SDS-polyacrylamide gel electrophoresis (SDS-PAGE) using a 10–15% gradient gel on the apparatus of FAST System from Pharmacia (Uppsala, Sweden). The molecular mass of the enzyme was estimated from the regression line of molecular weight markers as follows: phosphorylase b (94 kDa), albumin (67 kDa), ovalbumin (43 kDa), carbonic anhydrase (30 kDa), trypsine inhibitor (20.1 kDa), and α-lactalbumin (14.4 kDa).

In a fourth embodiment, the present invention relates to isolated polypeptides having immunochemical identity or partial immunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoectrophesis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophesis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the aminopeptidase activity of SEQ ID NO:2.

A polypeptide of the present invention may be obtained from microorganisms of any genus. For example, the polypeptide may be a gram positive bacterial polypeptide such as a Bacillus polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* polypeptide; or a Streptomyces polypeptide, e.g., a *Streptomyces lividans* or *Streptomyces murinus* polypeptide; or a gram negative bacterial polypeptide, e.g., an *E. coli* or a Pseudomonas sp. polypeptide.

In another preferred embodiment, the polypeptide is a Sphingomonas polypeptide such as a *Sphingomonas adhaesiva, Sphingomonas capsulata, Sphingomonas parapaucimobilis, Sphingomonas paucimobilis,* or *Sphingomonas yanoikuyae* polypeptide.

In a more preferred embodiment, the *Sphingomonas capsulata* polypeptide is a *Sphingomonas capsulata* IFO 12533 polypeptide, e.g., the polypeptide with the amino acid sequence of SEQ ID NO:2.

It will be understood that for the aforementioned species, the invention encompasses other taxonomic equivalents regardless of the species name by which they are known. Those skilled in the art will readily recognize the identity of appropriate equivalents. For example, *Sphingomonas capsulata* is also known as *Flavobacterium capsulatum, Sphingomonas paucimobilis* as *Flavobacterium devorans* and *Pseudomonas paucimobilis*, and Sphingomonas sp. as *Chromobacterium lividium*. See Yabuuchi et al., 1990, *Microbiol. Immunol.* 34: 99–119 for a discussion of the taxonomy of Sphingomonas.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-aminopeptidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO:1. In another more preferred embodiment, the nucleic acid sequence is the sequence contained in plasmid pMRT004.1-14 which is contained in *Escherichia coli* NRRL B-30032. In another more preferred embodiment, the nucleic acid sequence is the sequence encoding the mature polypeptide of SEQ ID NO:2 (i.e., amino acids 33 to 674) contained in plasmid pMRT004.1-14 which is contained in *Escherichia coli* NRRL B-30032. In another preferred embodiment, the nucleic acid sequence is nucleotides 670 to 2592 of SEQ ID NO:1, which encodes a mature polypeptide. The present invention also encompasses nucleic acid sequences which encode a polypeptide having the amino acid sequence of SEQ ID NO:2 or the mature polypeptide thereof, which differ from SEQ ID NO:1 by virtue of the degeneracy of the genetic code. The present invention also relates to subsequences of SEQ ID NO:1 which encode fragments of SEQ ID NO:2 which have phospholipase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 1572 nucleotides, more preferably at least 1722 nucleotides, and most preferably at least 1872 nucleotides.

The present invention also relates to mutant nucleic acid sequences comprising at least one mutation in the mature polypeptide coding region of SEQ ID NO:1, in which the mutant nucleic acid sequence encodes a polypeptide which consists of amino acids 33 to 674 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Sphingomonas, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO:1 (i.e., nucleotides 670 to 2592) of at least about 50%, preferably about 55%, preferably about 60%, preferably about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=3, gap penalty=3, and windows=20].

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for aminopeptidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under low stringency conditions, more preferably medium stringency conditions, even more preferably high stringency conditions, and most preferably very high stringency conditions, with a nucleic acid probe which hybridizes under the same conditions with the nucleic acid sequence of SEQ ID NO:1 or its complementary strand; or allelic variants and subsequences thereof (Sambrook et al., 1989, supra), as defined herein.

The present invention also relates to isolated nucleic acid sequences produced by (a) hybridizing a DNA with the sequence of SEQ ID NO:1, or its complementary strand, or a subsequence thereof, under low, medium, high, or very high stringency conditions; and (b) isolating the nucleic acid sequence. The subsequence is preferably a sequence of at least 100 nucleotides such as a sequence which encodes a polypeptide fragment which has aminopeptidase activity Methods for Producing Mutant Nucleic Acid Sequences The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of amino acids 33 to 674 of SEQ ID NO:2 or a fragment thereof which has aminopeptidase activity.

The introduction of a mutation into the nucleic acid sequence to switch one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The nucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Karnaroff et al., 1978, *Proceedings of the National Academy of Sciences USA* 75: 3727–3731), as well as the tac promoter (DeBoer et al., 1983, *Proceedings of National Academy of Sciences USA* 80: 21–25). Further promoters are described in "Useful proteins from recombinant bacteria" in *Scientific American*, 1980, 242: 74–94; and in Sambrook et al., 1989, supra.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109–137.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE) or the *Bacillus subtilis* neutral protease gene (nprT).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to is a chemical or physical stimulus, including the presence of a regulatory compound. Regulatory systems in prokaryotic systems would include the lac, tac, and trp operator systems. Other examples of regulatory sequences are those which allow for gene amplification. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli* and pUB110, pE194, pTA1060, and pAMβ1 permitting replication in Bacillus. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any unicellular microorganism, e.g., a prokaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus cirulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis,* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Sphingomonas, and more preferably *Sphingomonas capsulata*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence of SEQ ID NO:1 having at least one mutation in the nucleic acid sequence of SEQ ID NO:1, wherein the mutant nucleic acid sequence encodes a polypeptide having an amino acid sequence of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining aminopeptidase activity are known in the art. As described earlier, aminopeptidase activity is determined by measuring the initial rate of hydrolysis of the p-nitroanilide of alanine at 405 nm.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification* J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having aminopeptidase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889, a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941, the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93, or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588.

A promoter enhancer element may also be used to achieve higher expression of the enzyme in the plant. For instance, the promoter enhancer element may be an intron which is placed between the promoter and the nucleotide sequence encoding a polypeptide of the present inventiom. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having aminopeptidase activity of the present invention under conditions conducive for production of the polypeptide; and (b) recovering the polypeptide.

Removal or Reduction of Aminopeptidase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced aminopeptidase activity may be conveniently accomplished by modification or inactivation of a nucleic acid sequence necessary for expression of the polypeptide having aminopeptidase activity in the cell. The nucleic acid sequence to be modified or inactivated may be, for example, a nucleic acid sequence encoding the polypeptide or a part thereof essential for exhibiting aminopeptidase activity, or the nucleic acid sequence may have a regulatory function required for the expression of the polypeptide from the coding sequence of the nucleic acid sequence. An example of such a regulatory or control sequence may be a promoter sequence or a functional part thereof, I.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the aminopeptidase producing capability has been reduced. The mutagenesis, which may be specific or random, may be performed, for example, by use of a suitable physical or chemical mutagenizing agent, by use of a suitable nucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced aminopeptidase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, I.e., directly on the cell expressing the nucleic acid sequence to be modified, it is preferred that the modification be performed in vitro as exemplified below.

An example of a convenient way to inactivate or reduce production by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence encoding a polypeptide of the present invention may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention relates to a method for producing a protein product essentially free of aminopeptidase activity by fermentation of a cell which produces both a polypeptide of the present invention as well as the protein product of interest. The method comprises adding an effective amount of an agent capable of inhibiting aminopeptidase activity to the fermentation broth either during or after the fermentation has been completed, recovering the product of interest from the fermentation broth, and optionally subjecting the recovered product to further purification. This method is further illustrated in the examples below.

In a still further alternative aspect, the present invention relates to a method for producing a protein product essentially free of aminopeptidase activity, wherein the protein product of interest is encoded by a DNA sequence present in a cell encoding a polypeptide of the present invention. The method comprises cultivating the cell under conditions permitting the expression of the product, subjecting the resultant culture broth to a combined pH and temperature treatment so as to reduce the aminopeptidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a aminopeptidase inhibitor.

In accordance with this aspect of the invention, it is possible to remove at least 60%, preferably at least 75%, more preferably at least 85%, still more preferably at least 95%, and most preferably at least 99% of the aminopeptidase activity. It is contemplated that a complete removal of aminopeptidase activity may be obtained by use of this method.

The combined pH and temperature treatment is preferably carried out at a pH in the range of 6.5–7.5 and a temperature in the range of 40–60° C. for a sufficient period of time to attain the desired effect, where typically, 30 to 60 minutes is sufficient.

The methods used for cultivation and purification of the product of interest may be performed by methods known in the art.

The methods of the present invention for producing an essentially aminopeptidase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The aminopeptidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from aminopeptidase activity which is produced by a method of the present invention.

Uses

The polypeptides of the present invention may be used in the production of protein hydrolysates for enhancing the degree of hydrolysis and flavor development.

The polypeptides of the present invention may also be used to deactivate an enzyme.

Furthermore, a polypeptide of the present invention may be useful for a number of purposes in which a specific cleavage of peptide sequences is desirable. For instance, some proteins or peptides are synthesized in the form of inactive precursors comprising a number of additional amino acid residues at the N-terminal of the mature protein. A polypeptide of the present invention could provide the necessary post-translational processing to activate such precursor proteins.

Signal Peptide

The present invention also relates to nucleic acid constructs comprising a gene encoding a protein operably linked to a nucleic acid sequence consisting of nucleotides 574 to 669 of SEQ ID NO:1 encoding a signal peptide consisting of amino acids 1 to 32 of SEQ ID NO:2, wherein the gene is foreign to the nucleic acid sequence.

The present invention also relates to recombinant expression vectors and recombinant host cells comprising such a nucleic acid construct.

The present invention also relates to methods for producing a protein comprising (a) cultivating a recombinant host cell comprising a nucleic acid construct comprising a gene encoding a protein operably linked to a signal peptide coding region consisting of nucleotides 574 to 669 of SEQ ID NO:1, wherein the gene is foreign to the nucleic acid sequence, under conditions suitable for production of the protein; and (b) recovering the protein.

The nucleic acid sequence may be operably linked to foreign genes with other control sequences. Such other control sequences are described supra.

The protein may be any protein. Furthermore, the protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone, hormone variant, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source. For purposes of the present invention, the term "obtained from" as used herein in connection with a given source shall mean that the protein is produced by the source or by a cell in which a gene from the source has been inserted.

The present invention is further described by the following examples which should not be construed as limiting the scope of the invention.

EXAMPLES

Example 1

Production of Crude Enzyme Extract Powder from *Spingomonas capsulata*

*Sphingomonas capsulata* IFO 12533 was cultivated at 30° C. for 9 hours with aeration and agitation in a 5 liter fermentor containing 3 liters of medium composed of 0.5% sucrose, 1% gelatin, 0.5% yeast extract, 1% corn steep liquor, 0.3% NaCl, 0.2% $K_2HPO_4$, and 0.1% $MgSO_4.7H_2O$. The cell mass was collected from the culture broth and washed twice in 10 mM Tris-HCl pH 8.0 buffer yielding 43 g wet weight of cell mass. The cell mass was suspended in 200 ml of 10 mM Tris-HCl pH 8.0 buffer and lysed by adding lysozyme and Triton X-100 at final concentrations of 1 mg/ml and 0.1%, respectively, and incubating the solution at 37° C. for one hour. The solution was ultrasonicated and then centrifuged at 15,000×g for 10 minutes. The supernatant was recovered (200 ml) and protamine sulfate was added to a final concentration of 0.1% to precipitate nucleic acids. The precipitate was discarded through centrifugation in the same fashion, and the resulting solution was used as a crude enzyme extract.

The activity of the crude enzyme extract toward various synthetic peptides was determined as shown in Table 1. The results demonstrated that the crude enzyme extract possessed dipeptidyl peptidase IV, leucine aminopeptidase, glycine aminopeptidase, and prolyl oligopeptidase activity.

TABLE 1

Activities of various peptidase activities in the crude enzyme extract solution

| Peptidase | Substrate | Activity (%) |
| --- | --- | --- |
| prolyl oligopeptidase | Z-Ala-Ala-Pro-pNA | 46.0 |
| prolyl oligopeptidase | Z-Gly-Pro-NA | 68.7 |
| dipeptidyl peptidase IV | Gly-Pro-pNA | 21.9 |
| glycine aminopeptidase | Gly-pNA | 100 |
| leucine aminopeptidase | Leu-pNA | 67.8 |

The crude enzyme extract was precipitated by adding an equal volume of cold acetone. The enzyme precipitate was dissolved in a small volume of 10 mM phosphate pH 6.0 buffer and insoluble substances were removed by centrifugation. The enzyme was lyophilized to produce a crude enzyme powder.

Example 2

Purification of *Sphingomonas capsulata* Aminopeptidase I From Crude Enzyme Powder The crude enzyme powder described in Example 1 was dissolved in 20 mM phosphate pH 7.0 buffer and diluted until the conductivity of the sample was equivalent to the loading buffer, 20 mM phosphate pH 7.0. The sample was loaded onto a Pharmacia Q-Sepharose or Mono Q column pre-equilibrated with 20 mM phosphate pH 7.0 buffer. The flow-throughs from these columns were assayed for aminopeptidase activity with alanine-para-nitroanilide (Ala-pNA) using the procedure described below.

A stock solution of 100 mg of Ala-pNA per ml in dimethylsulfoxide was diluted with 50 mM sodium phosphate pH 7.5 buffer to a concentration of 2 mg per ml. The reaction of the aminopeptidase with the para-nitroanilide was initiated when a 10–50 µl aliquot of the enzyme solution was added to 200 µl of the substrate solution in a microtiter plate well. Analysis of initial rates of hydrolysis of the para-nitroanilide was monitored at 405 nm at room temperature in a THERMOmax Microplate Reader (Molecular Devices Corp., Sunnyvale, Calif., USA).

Aminopeptidase activity was present in the flow-through. The flow-through was concentrated using an Amicon Spiral Ultrafiltration System (Amicon, New Bedford, Mass., USA) equipped with a DIAFLO® PM 10 ultrafiltration membrane (Amicon, Inc., USA) and the pH of the concentrated flow-through was then adjusted to pH 6.0 using 70 MM sodium acetate pH 4.0 buffer.

The concentrated flow-through was applied to a Pharmacia Mono S 5/5 pre-packed 7×50 mm column (Pharmacia Biotech AB, Uppsala, Sweden) pre-equilibrated with 50 mM MES pH 6.0 buffer. Fractions were assayed as above for aminopeptidase activity. The bound aminopeptidase activity was eluted with a gradient from 0 to 0.2 M NaCl in 50 mM MES pH 6.0 buffer. The fractions with significant activity were then concentrated again using a PM 10 ultrafiltration membrane and then equilibrated in 50 mM phosphate pH 7.0 buffer containing 0.5 M ammonium sulfate.

The concentrated sample was then loaded onto a Phenyl Superose column pre-equilibrated with 50 mM phosphate pH 7.0 buffer containing 0.5 M ammonium sulfate. The enzyme was eluted with a gradient from 0.5 M ammonium sulfate containing 50 mM phosphate buffer to 50 mM phosphate buffer containing no ammonium sulfate. Active fractions were pooled.

SDS-PAGE analysis of the purified aminopeptidase revealed one band with a molecular weight of 67 kDa. The purified aminopeptidase was designated *Sphingomonas capsulata* aminopeptidase I.

Example 3

Purification of *Sphingomonas capsulata* Aminopeptidase I From Crude Enzyme Powder The crude enzyme powder described in Example 1 was dissolved in distilled water and loaded onto a CM Sepharose CL-6B column (Pharmacia Biotech, Uppsala, Sweden) pre-equilibrated with 15 mM sodium phosphate pH 6.0 buffer. Aminopeptidase I activity was eluted with a linear gradient of 15 mM to 60 mM sodium phosphate pH 6.0 buffer. Fractions of 7.4 ml were collected and assayed for aminopeptidase activity as described in Example 2.

Active fractions were pooled and dialyzed against 15 mM phosphate pH 6.0 buffer. The dialysate was sequentially loaded onto a hydroxylapatite column equilibrated with 15 mM sodium phosphate pH 6.0 buffer. Aminopeptidase I activity was eluted with a linear gradient of 15 mM to 300 mM sodium phosphate pH 6.0 buffer. Fractions were collected and assayed for aminopeptidase activity. Active fractions were pooled, dialyzed against distilled water, and lyophilized.

Example 4

Purification of *Sphingomonas capsulata* Aminopeptidase I

*Sphingomonas capsulata* aminopeptidase I was purified from a culture broth supernatant produced by cultivation of *Sphingomonas capsulata* strain IFO 12533 for 15 hours at 31° C., 250 rpm, and an initial pH of 7.45 in 1.5 liters of medium composed per liter of 10 g of bactopeptone, 5 g of yeast extract, 3 g of NaCl, 2 g of $K_2HPO_4$, 0.1 g of $MgSO_4.7H_2O$, and 5 g of glucose (autoclaved separately).

Aminopeptidase I activity was measured with alanine-para-nitroanilide (Ala-pNA) as described in Example 2.

The culture broth supernatant (approximately 1 liter) prepared by centrifugation, filtered using a Whatman glass microfiber filter (Whatman, Maidstone, England), filtered using Nalgene Filterware equipped with a 0.22 mm filter, and concentrated using an Amicon Spiral Ultrafiltration System equipped with a PM 10 ultrafiltration membrane was equilibrated with 10 mM sodium phosphate pH 6.0 buffer until the conductivity and pH were equal to the loading buffer, 50 mM MES pH 6.0. The filtered solution was loaded onto a 24×390 mm column containing approximately 180 ml of SP-Sepharose, Fast Flow (Pharmacia Biotech AB, Uppsala, Sweden) pre-equilibrated with 50 mM MES pH 6.0 buffer. Protein with aminopeptidase I activity was eluted with a 240 ml gradient from 0 to 0.2 M NaCl in 50 mM MES pH 6.0 buffer. Fractions with aminopeptidase I activity were pooled, desalted using a PM 10 membrane, and equilibrated with 20 mM sodium phosphate pH 7.0 buffer.

The pooled solution was then loaded onto a Pharmacia MonoQ Beads column pre-equilibrated with 20 mM sodium phosphate pH 7.0 buffer. Protein with aminopeptidase I activity did not bind to the column and was collected in the flow-through. The flow-through was concentrated using a PM 10 membrane system as above, and the pH adjusted to 6.0 with 70 mM sodium acetate pH 4.0 buffer.

The concentrated flow-through was loaded onto a Pharmacia Mono S column pre-equilibrated with 50 mM MES pH 6.0 buffer. The aminopeptidase was eluted with a 60 ml gradient from 0 to 0.2 M NaCl in 50 mM MES pH 6.0 buffer. The fractions with significant Ala-pNA activity were then pooled, concentrated, and equilibrated with 50 mM phosphate pH 7.0 buffer containing 0.5 M $(NH_4)_2SO_4$ using a PM 10 membrane as above.

Finally, the concentrated sample was loaded onto a Pharmacia Phenyl Superose 5/5 pre-packed 7×50 mm column (Pharmacia Biotech AB, Uppsala, Sweden) pre-equilibrated with 50 mM phosphate pH 7.0 buffer containing 0.5 M $(NH_4)_2SO_4$. Protein with aminopeptidase I activity was then eluted with a 30 ml gradient from 0.5 to 0 M $(NH_4)_2SO_4$ in 50 mM phosphate pH 7.0 buffer. Fractions containing aminopeptidase I activity were analyzed by SDS-PAGE and then pooled.

SDS-PAGE analysis of the purified *Sphingomonas capsulata* aminopeptidase I revealed one band with a molecular weight of 67 kDa.

Example 5

Amino Acid Sequencing of *Sphingomonas capsulata* Aminopeptidase I (67 kDa)

Samples of the purified *Sphingomonas capsulata* aminopeptidase I described in Example 2 were electrophoresed using a 8–16% Tris-glycine SDS-polyacrylamide gel and subsequently blot-transferred to a PVDF membrane using 10 mM CAPS (3-[cyclohexylamino]-1-propanesulfonic acid) pH 11 in 10% methanol for 2 hours. The PVDF membrane was stained with 0.1% Coommassie Blue R-250 in 40% methanol/1% acetic acid for 20 seconds and destained in 50% ethanol to observe the protein bands. The major band of 67 kDa was excised and subjected to amino terminal sequencing on an Applied Biosystems Model 476A Protein Sequencer using a blot cartridge and liquid phase TFA delivery according to the manufacturers instructions. The protein was found to be N-terminally blocked to Edman sequencing chemistry.

A 1.0 ml sample of the purified aminopeptidase I described in Example 2 was dried on a Savant Speed Vac AS160 and then reconstituted with 300 µl of 70% formic acid (aqueous). A few crystals of cyanogen bromide were added and incubated at room temperature in the dark overnight. The sample was redried in the Speed Vac and reconstituted in Tricine sample buffer (Novex, San Diego, Calif., USA). The cyanogen bromide cleavage fragments were separated using a 10–20% Tricine SDS-polyacrylamide gel into bands of 42, 30, 17, 15, 10, 6, and 4 kDa and blot-transferred to a PVDF membrane. The 6, 10, 15, 17, 30, and 42 kDa bands were excised and subjected to amino terminal sequencing. N-terminal sequences of the 15, 10, and 6 kDa bands were obtained showing the following sequences:

The purified aminopeptidase was also partially digested with Endoproteinase Glu-C as follows: 7.5 µl of 0.125 M Tris-HCl pH 6.7 containing 2.5% SDS was added to 60 µl of concentrated aminopeptidase in 0.125 M Tris-HCl pH 6.7. The sample was mixed, boiled for 2 minutes, and then cooled at 23° C. for 15 minutes. Then 10 µl of Endoproteinase Glu-C Sequencing Grade (Boehringer Mannheim, Indianapolis, Ind.) at a concentration of 400 µg/ml in 0.125 M Tris-HCl pH 6.7 was added. The sample was incubated for 2 hours at 37° C. After the incubation, 45 µl of 2× Tricine SDS Sample buffer (Novex, San Diego, Calif., USA) was added and the sample was boiled for 5 minutes.

Peptide fragments were separated using 10–20% Novex Tris-tricine gels under reducing conditions. Peptide bands were observed excised at 40, 30, 25, 22, 20, 17, 10, 6, 5, and 4 kDa Sequencing of the 40, 30, and 10 kDa bands revealed they were very mixed. The 17 and 22 kDa bands were mixed but with a major sequence of FKDEPNPYDKAR-MADAKVLSLFNSLGVTLDKDGKV corresponding to amino acids 532 to 566 of SEQ ID NO:2.

Example 6

Characterization of *Sphingomonas capsulata* Aminopeptidase I (67 kDa)

Stock solutions of 100 mg of each para-nitroanilide per ml of dimethylsulfoxide were diluted with 50 mM sodium phosphate pH 7.5 buffer to concentrations of 2 mg per ml. Where the substrates were incompletely soluble, their suspensions were used (shown with an asterisk in Table 2 below). The reaction of the *Sphingomonas capsulata* aminopeptidase I with each para-nitroanilide was initiated when a 10 µl aliquot of the enzyme solution in 50 mM sodium phosphate pH 7.0 buffer was added to 190 µl of a substrate solution in a 96 well microtiter plate. Analysis of initial rates of hydrolysis of the para-nitroanilides was monitored at 405 nm and 25° C. in a THERMOmax Microplate Reader (Molecular Devices Corp., Sunnyvale, Calif., USA). The results (Table 2) showed that the aminopeptidase I preferably hydrolyzed Ala-pNA, but also hydrolyzed Gly-pNA. However, among the dipeptide substrates the aminopeptidase I hydrolysed Gly-Phe-pNA more quickly than Ala-Ala-pNA.

TABLE 2

Substrate specificity of *Sphingomonas capsulata* aminopeptidase I

| Amino acid p-nitroanilides | Relative activity (%) |
|---|---|
| Ala | 100 |
| Met | 24 |
| Gly* | 20 |
| Leu | 18.5 |
| Glu* | 6 |
| Asp | 4.5 |
| Lys | 6 |
| Ile | 0.5 |
| Val | 0.5 |

| 15 kDa: | AVPIAHGVPDAQDVPYPG | (corresponding to amino acids 43 to 61 of SEQ ID NO:2) |
| 10 kDa: | AVNGDAYDADKLKGAITNAKTGNPGAGRPI | (corresponding to amino acids 588 to 617 of SEQ ID NO:2) |
| 6 kDa: | GSIGLEHHRSSENQQEPKSLTDWAA | (corresponding to amino acids 303 to 327 of SEQ ID NO:2) |

TABLE 2-continued

Substrate specificity of *Sphingomonas capsulata* aminopeptidase I

| Amino acid p-nitroanilides | Relative activity (%) |
|---|---|
| Phe* | 0 |
| Pro | 0 |

The pH optimum for the 67 kDa aminopeptidase I was determined using the following protocol. The buffer solutions at different pH's were prepared by adding distilled water to 4.25 g of sodium acetate and 3.78 g of Tris (free base) to a final volume of 250 ml and adjusting the pH to 8.5, 8.0, 7.5, 7.0, 6.5, 5.80, 5.5, and 5.0 with 36.5–38% HCl. Aliquots of 10 ml were removed at each pH. A 20 μl volume of a 100 mg/ml solution of Ala-pNA in DMSO was added to 980 μl of each buffer solution. The pH was then determined to be 8.5, 8.0, 7.57, 7.30, 7.09, 6.68, 6.14, and 5.25 for the buffer solutions after the addition of the substrate. Another solution of substrate at a concentration of 2 mg/ml was prepared at the various pHs. The reaction was initiated by the addition of 10 μl of enzyme solution, diluted 5-fold in 10 mM Tris-HCl pH 7.5, to 200 μl of substrate at the various pHs at room temperature and monitored at 405 nm.

The results shown in Table 3 demonstrated that aminopeptidase I has a pH optimum in the range of 5.3 to 8.5, and more preferably in the range of 7.0 to 7.5 (see FIG. 1). There was no detectable autohydrolysis of Ala-pNa in the pH range 5.25–8.5. At pH 5.5, hydrolysis of Ala-pNA catalyzed by aminopeptidase I did not follow Michaelis-Menten kinetics where the apparent $K_m$ and $V_{max}$ had negative values due to the activation of the enzyme by a substrate. At pH 7.5, the $K_m$ was 2.5 mM.

TABLE 3 pH profile of *Sphingomonas capsulata* aminopeptidase I

| pH | Relative Activity (%) |
|---|---|
| 5.25 | 24.9 |
| 6.14 | 56.4 |
| 6.68 | 78.4 |
| 7.09 | 99.4 |
| 7.30 | 100 |
| 7.57 | 92.8 |
| 8.0 | 61 |
| 8.49 | 24.2 |

Figure 2:
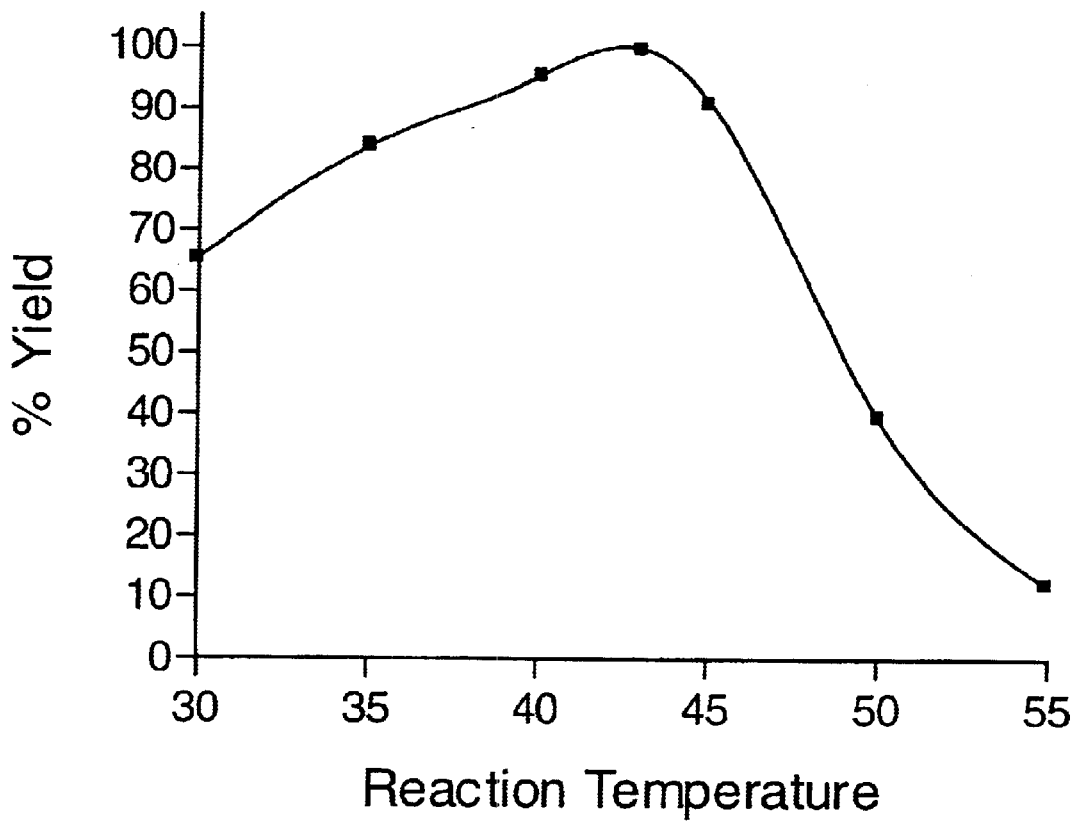
FIG. 2 shows the activity of a *Sphingomonas capsulata* aminopeptidase versus the temperature in 50 mM sodium phosphate buffer pH 7.5.

The temperature optimum was determined using Ala-pNA as substrate in 50 mM sodium phosphate pH 7.5 buffer over the temperature range of 30° C. to 55° C. The results showed that the aminopeptidase I has a temperature optimum in the range of 35° C. to 46° C., and more preferably in the range of 40° C. to 45° C. at pH 7.5 (see FIG. 2).

Figure 3:
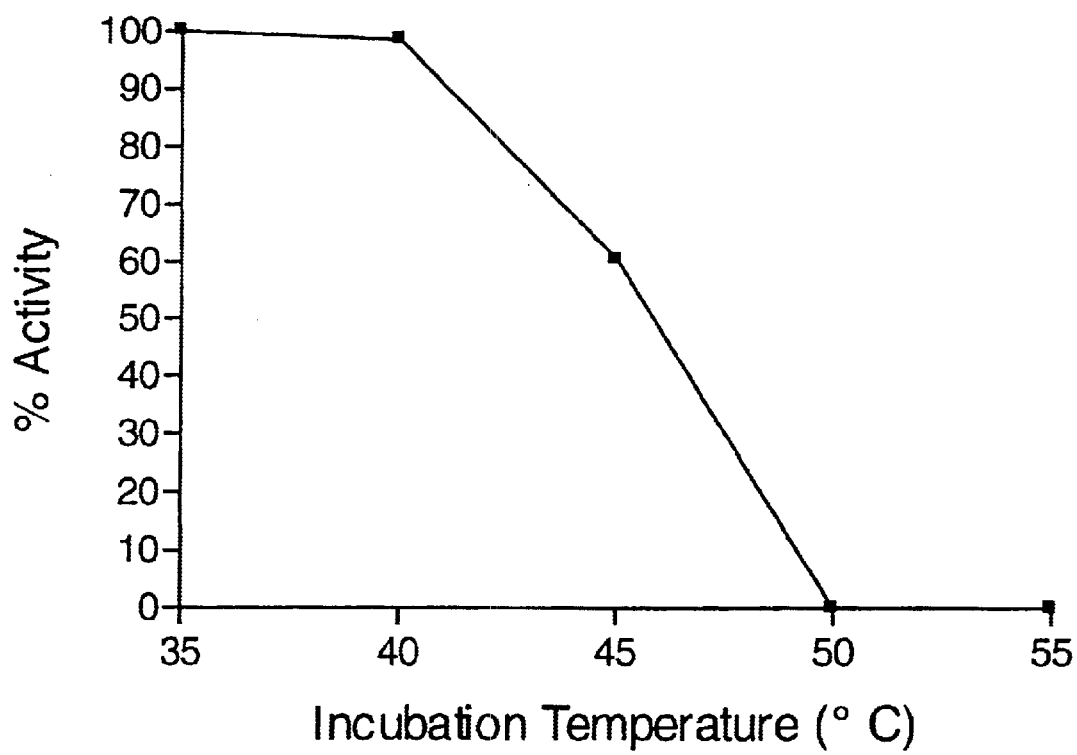
FIG. 3 shows the activity of a *Sphingomonas capsulata* aminopeptidase versus the temperature in 50 mM sodium phosphate buffer pH 7.5.

The temperature stability of aminopeptidase I was determined by incubating the enzyme for 20 minutes in 50 mM sodium phosphate pH 7.5 buffer at temperatures in the range of 35° C. to 55° C. followed by cooling on ice and measuring the residual activity using Ala-pNA as substrate at pH 7.5 as described above. The results showed (see FIG. 3) that the aminopeptidase I was approximately 100% stable up to 40° C. at pH 7.5. At 45° C., the enzyme retained approximately 60% residual activity, while at 50° C. the enzyme was completely inactivated.

Example 7

Comparison Between DH Increasing Effect of Crude and Purified *Sphingomonas capsulata* Aminopeptidase I The DH increasing effect of *Sphingomonas capsulata* aminopeptidase I (67 kDa) was evaluated in soy protein hydrolysis and compared to the performance of the crude enzyme powder prepared as described in Example 1.

The degree of hydrolysis (DH) of the soy protein was determined as follows. The DH, defined as described in by Adler-Nissen (1986, *Enzymic Hydrolysis of Food Proteins*, Elsevier Applied Science Publishers), was determined by reaction of the supernatant with OPA (ortho-phthaldialdehyde, Sigma Chemical Co., St. Louis, Mo.) essentially as described by Church et al., 1983, *Journal of Dairy Science* 66: 1219–1227 with correction factors as determined by Adler-Nissen, 1979, *Agricultural and Food Chemistry* 27: 1256–1262.

The aminopeptidase I was added in increasing dosage to either a low-background (1.5% of the substrate protein) or a high background (6% of the substrate protein) of FLAVOURZYME 1000L™ and a dosage of ALCALASE 2.4L® of 1.5% of the substrate protein. The experiments were carried out as described below:

Hydrolysis was carried out on a 10 ml scale at 50° C. for 18 hours. The initial pH was 7 with no pH readjustment during hydrolysis. Inactivation of the enzyme was carried out at 85° C. for 3 minutes in a water bath. The substrate concentration was 2% protein from soy bean meal. The substrate was heat treated in a water bath at 85° C. for 3 minutes. The enzymes used with FLAVOURZYME 1000L™ and ALCALASE 2.4L® described above were crude *Sphingomonas capsulata* aminopeptidase I powder (see Example 1) and the purified *Sphingomonas capsulata* aminopeptidase I described in Example 4.

The aminopeptidase I dosages used were based on alanyl-aminopeptidase units (AAU) determined by the hydrolysis of Ala-pNa at pH 7.5. One AAU unit of the aminopeptidase I is defined as the quantity of an enzyme which hydrolyses 1.0 micromole of Ala-pNa per minute in a 9.1 mM solution of Ala-pNa at pH 7.5, 22° C., and ionic strength=0.05.

The specific activity of the purified aminopeptidase I was approximately 12 AAU/mg enzyme. Therefore, a dosage of 0.24 AAU per 200 mg soy protein, for example, corresponded to 0.1 g enzyme per kg soy protein.

Figure 4:
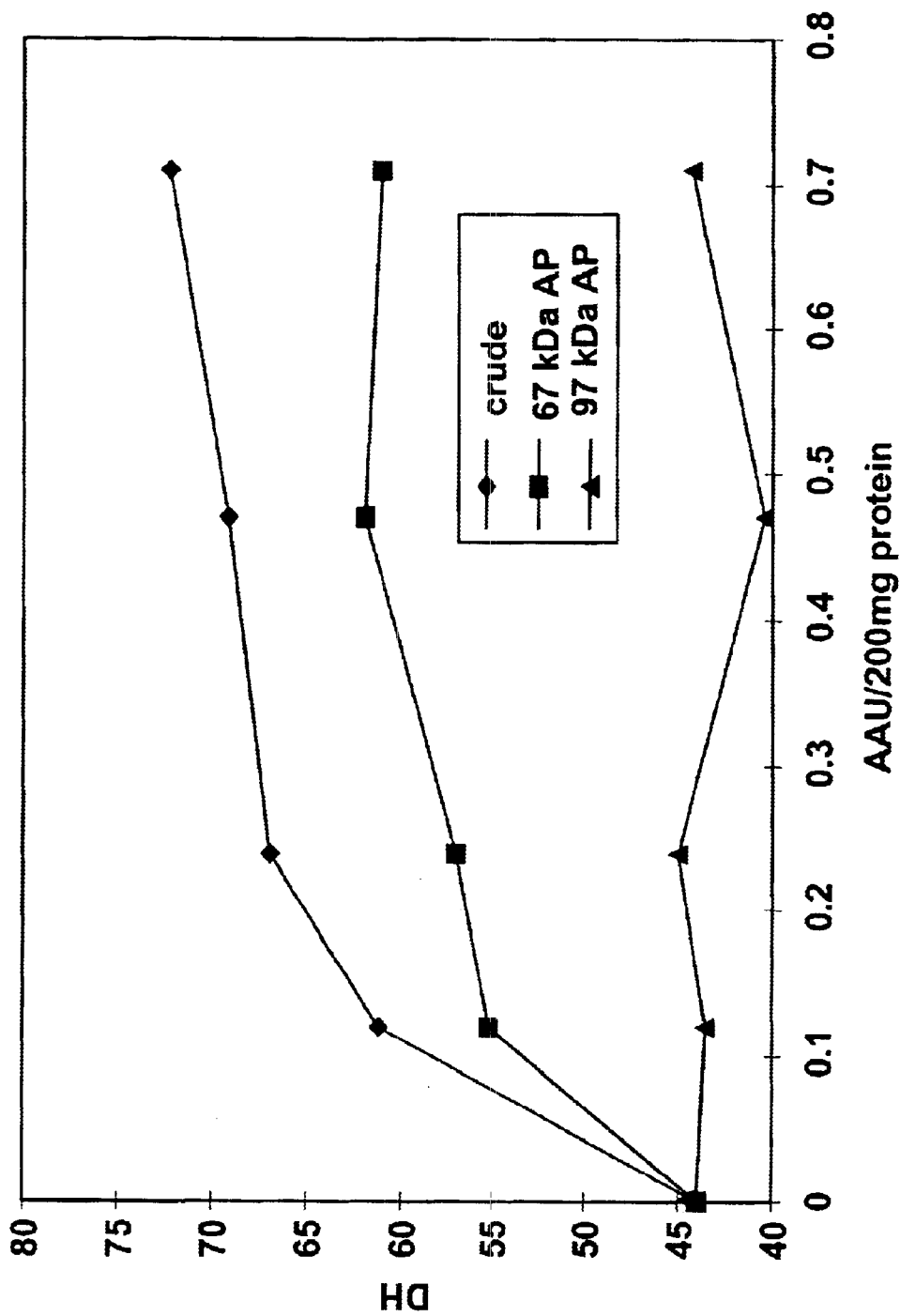
FIG. 4 shows the effect on the DH when adding a *Sphingomonas capsulata* crude enzyme extract and a *Sphingomonas capsulata* aminopeptidase to respectively low and high Flavourzyme™ background dosage.
Figure 5:
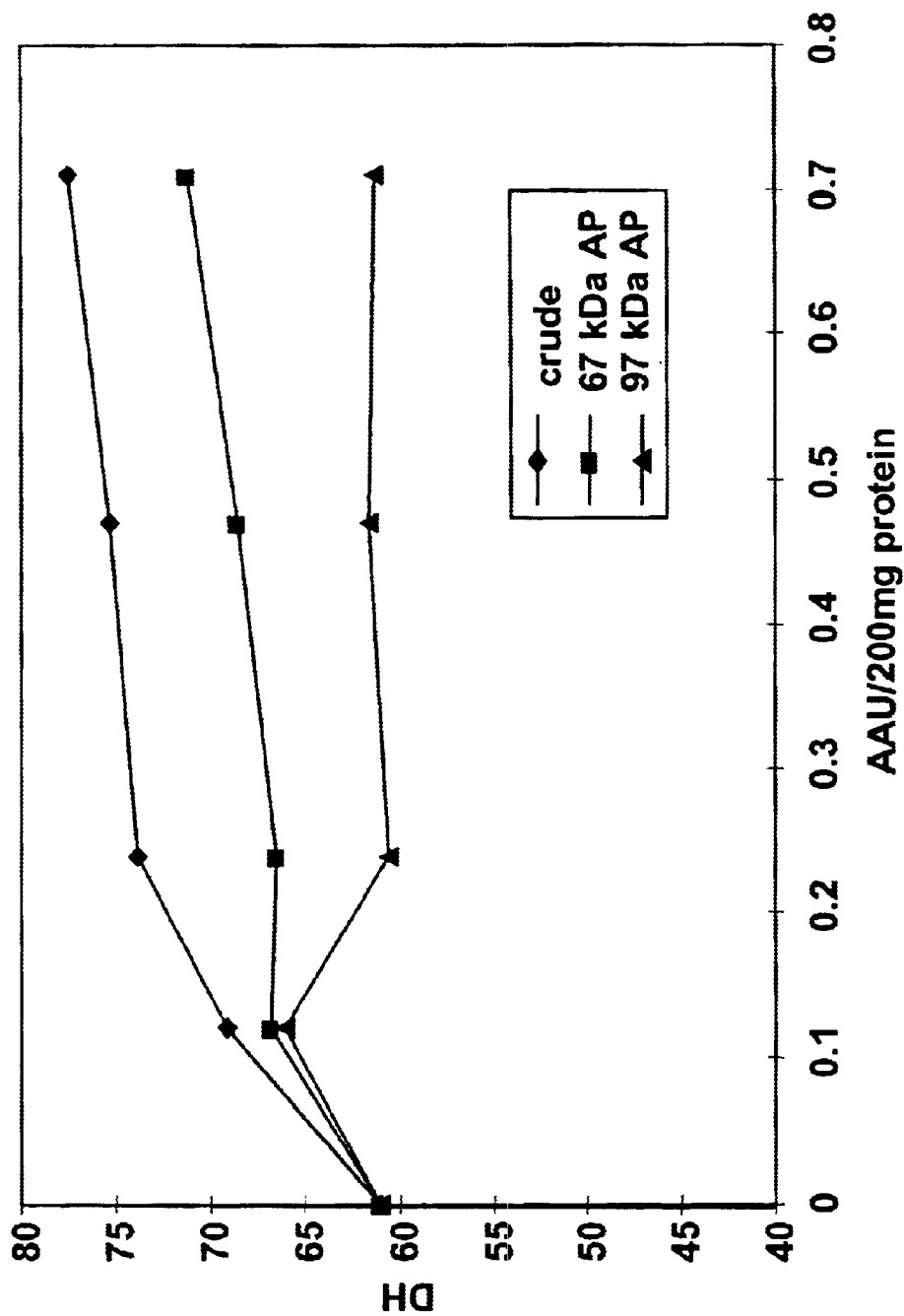
FIG. 5 shows the effect on the DH when adding a *Sphingomonas capsulata* crude enzyme extract and a *Sphingomonas capsulata* aminopeptidase to respectively low and high Flavourzyme™ background dosage.

The DH as function of dosage of AAU is shown in FIG. 4 for low background dosages of FLAVOURZYME™ and in FIG. 5 for a high background dosage of FLAVOURZYME™.

FIGS. 4 and 5 show that the hydrolysates were close to being saturated with aminopeptidase I activity at the highest dosages of AAU. The crude enzyme was capable of increasing DH from 44% to 72% when added to a low dosage of FLAVOURZYME™. The purified aminopeptidase I increased DH to 61–62%. Thus, the purified aminopeptidase I was responsible for (62–44)/(72–44)×100%=64% of the DH increasing effect of the crude enzyme. The crude enzyme increased DH from 61% to 77% when added to a high dosage of FLAVOURZYME™. The purified aminopeptidase I increased DH to 71%. Thus, the purified aminopeptidase I was responsible for (71–61)/(77–61)× 100%=63% of the increasing effect of the crude enzyme.

An alternative to addition of aminopeptidase I is the addition of more FLAVOURZYME™. The addition of 0.5% extra FLAVOURZYME™ to the background dosage of 1.5% increased DH from 44% to 48%. The effect of adding aminopeptidase I was calculated to be (62–48)/(72–48)× 100%=58% of the effect of the crude enzyme.

Likewise, addition of 1% extra FLAVOURZYME™ to the background dosage of 6% FLAVOURZYME™ increased DH from 61% to 63%. The effect of the aminopeptidase I was calculated to be (71–63)/(77–63)×100%= 57% of the effect of the crude enzyme.

The highest DH obtained was 77%. The DH value was based on total protein and not on soluble protein. The protein solubility was around 85%. Therefore, DH in the soluble protein was around 91%, which was very close to 100%.

The % relative increase in the individual free amino acids (FAA) due to AAU additions are shown in Table 4. Hyp, methioninsulphonic acid, and Trp were not included in the Table due to very fluctuating and uncertain results.

The enzymes used with FLAVOURZYME™ and ALCALASE® were crude *Sphingomonas capsulata* aminopeptidase I powder and purified *Sphingomonas capsulata* aminopeptidase I as in Example 7. Glycine aminopeptidase unit (GAPU) of both crude and purified enzyme was measured in 50 mM Tris-HCl pH 7.5 buffer at 37° C. using Gly-pNA as

TABLE 4

% Relative increase in FAA due to addition of aminopeptidases

| FAA | 1.5% FLAVOURZYME ™ +crude | 6.0% FLAVOURZYME ™ +67 kDa AP | 1.5% FLAVOURZYME ™ +crude | +67 kDa AP | +67 kDa AP versus 6.0% FLAVOURZYME ™ |
|---|---|---|---|---|---|
| Asp | 250.3 | 164.5 | 74.8 | 24.8 | 24.2 |
| Glu | 195.6 | 145.9 | 70.7 | 31.3 | 28.7 |
| Asn | 80.5 | 32.3 | 36.9 | 7.6 | -15.2 |
| Ser | 149.5 | 69.3 | 78.7 | 41.7 | 12.5 |
| Gln | 198.6 | 138.9 | 51.6 | 28.1 | 9.9 |
| Gly | 353.6 | 305.7 | 117.4 | 92.9 | 90.6 |
| His | 64.0 | 30.3 | 18.8 | 7.5 | -6.8 |
| Arg | 59.6 | 37.4 | 18.1 | -31.4 | -2.9 |
| Thr | 84.3 | 34.7 | 21.2 | 2.4 | -18.3 |
| Ala | 200.2 | 130.3 | 71.2 | 36.5 | 27.3 |
| Pro | 73.2 | 32.4 | -9.0 | -11.5 | -39.7 |
| Tyr | 75.4 | 47.6 | 13.8 | 8.5 | -6.9 |
| Val | 114.1 | 44.0 | 32.5 | 6.3 | -17.7 |
| Met | 47.9 | -20.0 | 42.5 | 21.1 | -46.7 |
| Cys | 5.0 | 12.6 | 17.5 | 9.5 | 6.3 |
| Ile | 133.6 | 48.7 | 34.0 | 7.2 | -21.0 |
| Leu | 67.4 | 35.2 | 16.4 | 5.2 | -9.1 |
| Phe | 62.6 | 41.8 | 13.3 | 7.2 | -4.5 |
| Lys | 105.5 | 62.4 | 28.2 | 13.8 | -1.4 |
| total | 110.1 | 64.5 | 36.9 | 10.3 | 0.0 |
| DH | 59.6 | 34.8 | 24.4 | 14.2 | -2.2 |

The results showed that when the crude or purified *Sphingomonas capsulata* aminopeptidase I was added, Gly was the amino acid which showed the highest increase. Other amino acids, which showed increased release were Ala, Glu, Gln, Asp and Ser, but for these amino acids the crude enzyme appeared to release more than the purified aminopeptidase I alone probably due to the presence of other aminopeptidases in the crude enzyme.

A high DH hydrolysate was produced by use of a high dosage of FLAVOURZYME™. The same high DH and release of FAA were obtained by using a low dosage of FLAVOURZYME™ supplemented with 67 kDa aminopeptidase I or the crude enzyme. According to Table 4, a hydrolysate obtained by use of a low dosage of FLAVOURZYME™ supplemented with 67 kDa aminopeptidase I will have a higher level of especially Gly, but also Ala, Glu and Asp and a lower level of Met, Pro and Ile as compared with hydrolysates obtained by using a high dosage of FLAVOURZYME™ alone.

Example 8

DH Increasing Effect of *Sphingomonas capsulata* Aminopeptidase I in Gelatin Hydrolysis The DH increasing effect of the *Sphingomonas capsulata* aminopeptidase I was tested in gelatin hydrolysis.

The aminopeptidase I was added in increased dosage to either a low or a high background of FLAVOURZYME™ and ALCALASE® as performed in Example 7.

Hydrolysis was carried out in 200 μl reactions in Eppendorf tubes. The substrate gelatin (Merck) was dissolved in distilled water at 85° C. for 5 minutes. After cooling to 50° C., the pH was adjusted to 6.5. The final gelatin concentration was adjusted to 2% after the addition of enzymes. The substrate concentration in each reaction was calculated to be 4 mg.

a substrate. Aminopeptidase I was assayed at 37° C. in 50 mM Tris-HCl (pH 7.5). Gly-pNA (Bachem Feinchemikalien AG, Bubendorf, Switzerland) was dissolved in 40% dioxane at a concentration of 2.5 mg/ml and 1.5 volume of 50 mM Tris-HCl (pH 7.5) was added to a substrate concentration of 1 mg/ml. The enzyme sample was diluted in 500 μl of the same buffer and 100 μl of the substrate solution was added and incubated at 37° C. for 5 minutes. The reaction was terminated by the addition of 300 μl of 1 M sodium acetate pH 4.0 buffer. For the blank reaction, the stop solution was added to the enzyme solution and incubated for 5 minutes at 37° C., and then the substrate solution was added. The absorbance at 410 nm was measured for both the sample and blank reactions. The enzyme activity was calculated using the molecular extinction coefficient at 410 nm for pNA as 9480 $M^{-1}$ $cm^{-1}$. One unit of GAPU was defined as the quantity of enzyme that hydrolyses 1 micromole of Gly-pNA at 37° C. per minute under the conditions described above. The specific activities of the crude and purified aminopeptidase I used were 0.725 GAPU/mg and 6.45 GAPU/mg, respectively. The enzymes were dosed to the 4 mg protein according to the scheme in Table 5.

TABLE 5

| Tube no. | FLAVOURZYME ™ (μg) | ALCALASE ® (μg) | Aminopeptidase I (μg) |
|---|---|---|---|
| 1 | 80 (2%) | 40 (1%) | |
| 2 | " | " | |
| 3 | " | " | |
| 4 | " | " | |
| 5 | " | " | 8 (0.2%) ≈ 0.05 U |
| 6 | " | " | 31 (0.77%) ≈ 0.2 U |
| 7 | " | " | 78 (2%) ≈ 0.5 U |
| 8 | " | " | 155 (4%) ≈ 1.0 U |

TABLE 5-continued

| Tube no. | FLAVOURZYME ™ (µg) | ALCALASE ® (µg) | Aminopeptidase I (µg) |
|---|---|---|---|
| 9 | 280 (7%) | 40 (1%) | |
| 10 | " | " | |
| 11 | " | " | |
| 12 | " | " | |
| 13 | " | " | 8 (0.2%) ≈ 0.05 U |
| 14 | " | " | 31 (0.77%) ≈ 0.2 U |
| 15 | " | " | 78 (2%) ≈ 0.5 U |
| 16 | " | " | 155 (4%) ≈ 1.0 U |

Enzyme/substrate ratios are given in parentheses after amounts of enzymes shown as weight.

The hydrolysis reactions were performed at 50° C. for 18 hours. Enzymes were inactivated at 85° C. for 5 minutes followed by centrifugation. DH was calculated on the basis of the total protein content of hydrolysate using the OPA method.

Figure 6:
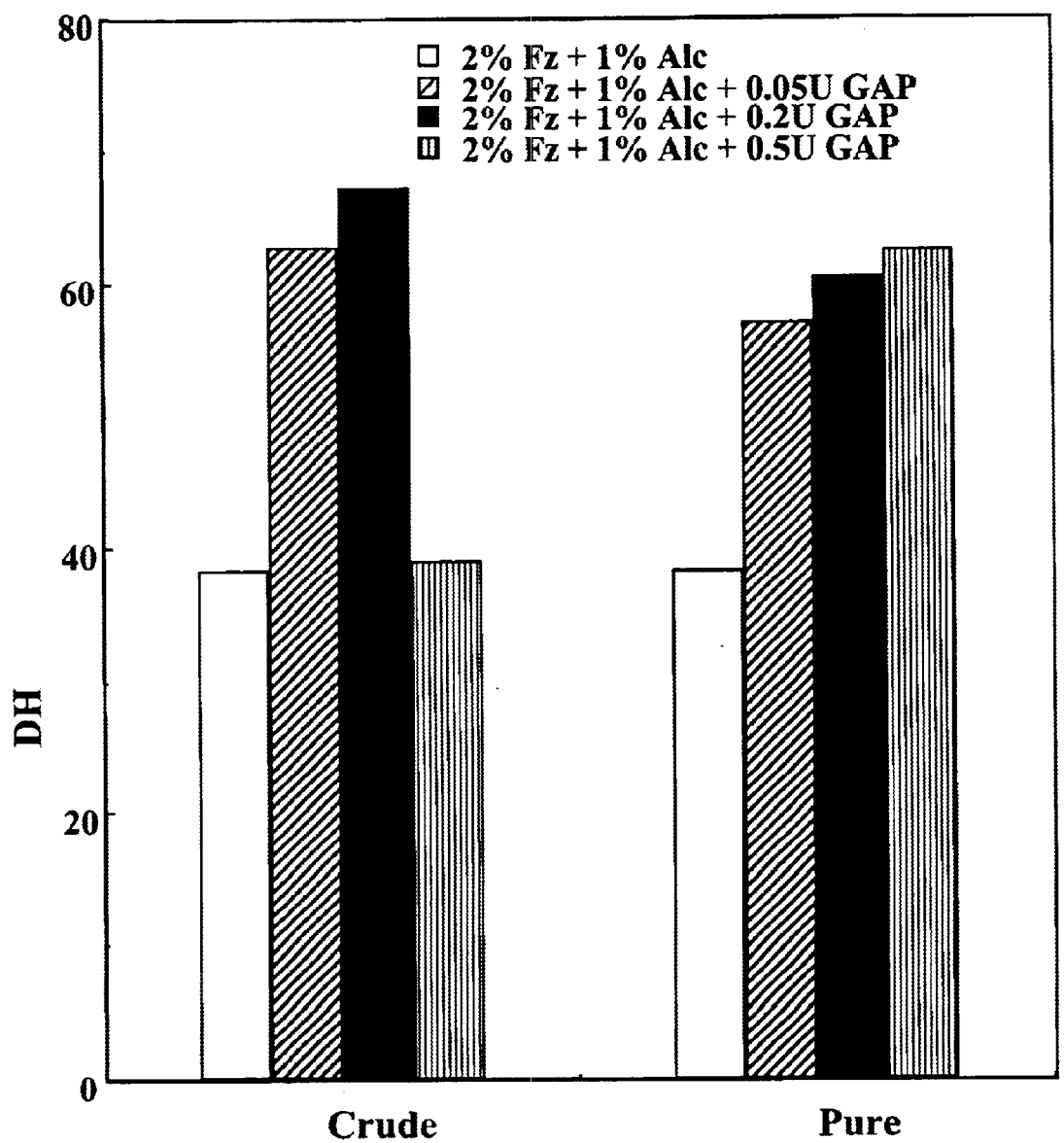
FIG. 6 shows the DH obtained by different combinations of Flavourzyme™, Alcalase® and a *Sphingomonas capsulata* aminopeptidase.
Figure 7:
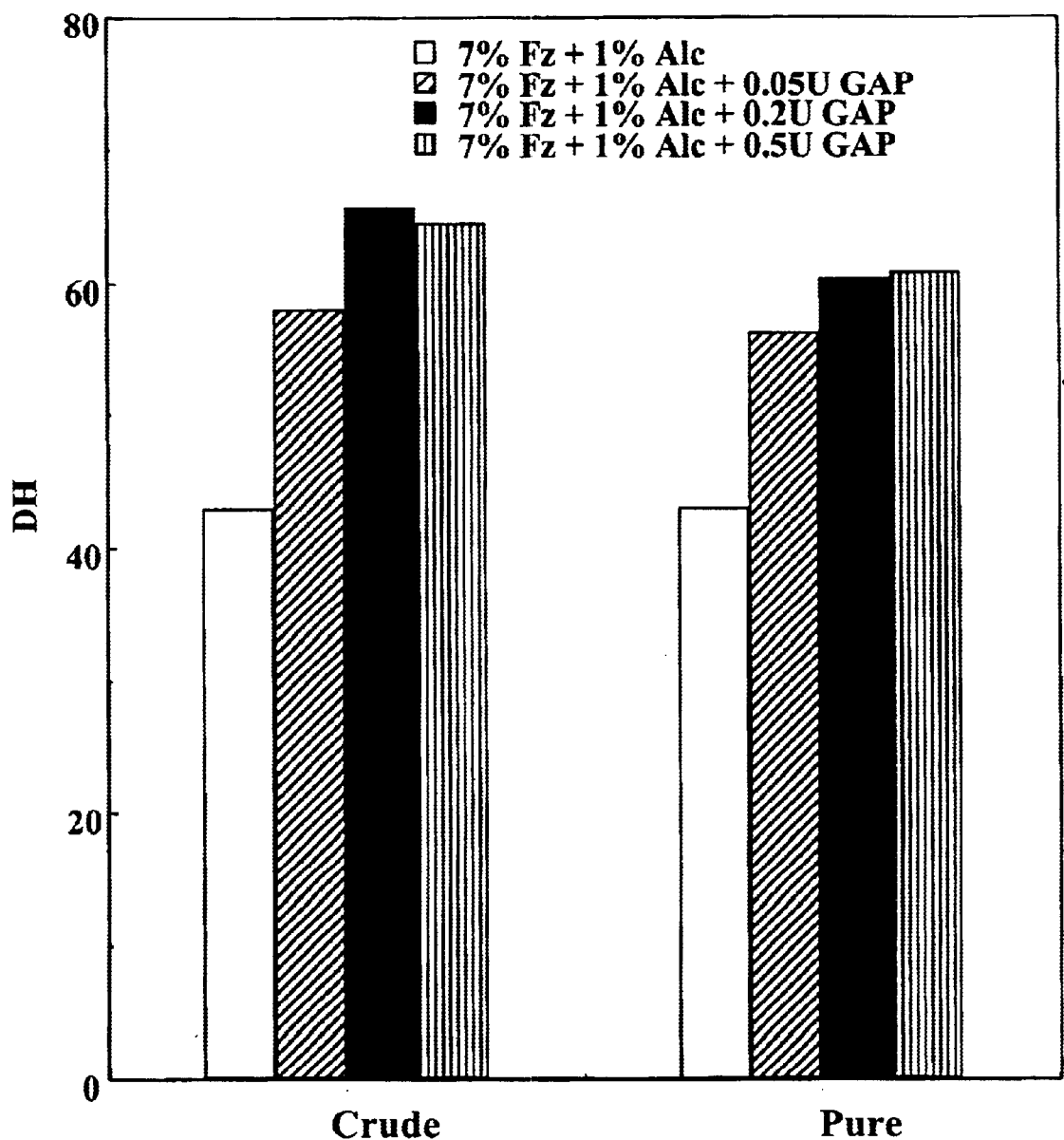
FIG. 7 shows the DH obtained by different combinations of Flavourzyme™, Alcalase® and a *Sphingomonas capsulata* aminopeptidase.

The DH-increasing effect of purified aminopeptidase I shown in FIGS. 6 and 7 demonstrated that addition of the crude and the purified enzyme (0.2 U/4 mg gelatin) to the low FLAVOURZYME™ background increased DH from 38% to 67% and 61%, respectively. The DH increasing effect was almost saturated at this dose.

When the dose of FLAVOURZYME™ was increased up to 7%, the control DH increased to 43%. However, the DH obtained with purified aminopeptidase I was 61% which almost coincided with those obtained in the low FLAVOURZYME™ background.

These results indicated that the *Sphingomonas capsulata* aminopeptidase I hydrolyses proteins to an extremely high DH. Furthermore, using aminopeptidase I, the dosage of other proteolytic enzymes can be reduced to obtain the same DH.

Example 9

Preparation of Probes for *Sphingomonas capsulata* B46 Aminopeptidase I Gene Identification Based on internal amino acid sequences of the *Sphingomonas capsulata* B46 aminopeptidase I shown below, degenerate primers were synthesized to amplify probes via the polymerase chain reaction (PCR) to identify the *Sphingomonas capsulata* B46 aminopeptidase I gene.

| Internal peptide AB0713: | AVNGDAYDADKLKGAITNAKTGNPGAGRPI | (corresponding to amino acids 588 to 617 of SEQ ID NO:2) |
|---|---|---|
| Internal peptide AB0781: | FKDEPNPYDKARMADAKVLSLFNSLGVTLDKDGKV | (corresponding to amino acids 532 to 566 of SEQ ID NO:2) |

The primers designated 550-39-1, 550-23-4, and 550-39-2 shown below were used in the amplification reactions described below.

```
550-23-4:  5'-gcrtcrtangcrtcncc-3'      (SEQ ID NO:3)
550-39-1:  5'-aargaygarccnaaycc-3'      (SEQ ID NO:4)
550-39-2:  5'-acyttytcrtcyttrtc-3'      (SEQ ID NO:5)
```

Amplification reactions were prepared in 50 µl volume with 50 pmol of either primers 550-39-1 and 550-23-4 or 550-39-1 and 550-39-2, 1 µg of *Sphingomonas capsulata* B46 chromosomal DNA as template, 1×PCR buffer (Perkin-Elmer, Foster City, Calif.), 200 (M each of dATP, dCTP, dGTP, and dTTP, and 0.5 U of AmpliTaq Gold (Perkin-Elmer, Foster City, Calif.). *Sphingomonas capsulata* B46 chromosomal DNA was isolated using the Bacterial Isolation Protocol described in the Qiagen Genomic Handbook (Qiagen, Inc., Chatsworth, Calif.). Reactions were incubated in a Stratagene Robocycler 40 (Stratagene, La Jolla, Calif.) programmed for 1 cycle at 95° C. for 10 minutes, 35 cycles each at 95° C. for 1 minute, 44° C. for 1 minute, and 72° C. for 1 minute, and 1 cycle at 72° C. for 7 minutes.

Amplification with primers 550-39-1 and 550-39-2 resulted in a 100 bp product designated 100 bp, and with primers 550-39-1 and 550-23-4 a 191 bp product designated 191 bp. Both PCR products were individually cloned into the vector pCR2.1/TOPO from the TOPO/TA Cloning Kit (Invitrogen, Inc., La Jolla, Calif.) according to the manufacturer's instructions. Sequencing with an Applied Biosystems Model 377 Sequencer (Applied Biosystems, Foster City, Calif.) showed that the sequence of the 100 bp product was contained within the 191 bp product indicating that amino acid sequence AB0713 lay approximately 30 amino acids upstream of amino acid sequence AB0781.

A new set of non-degenerate primers designated 550-71-2 and 550-79-1, described below, were then used to PCR-amplify DIG-labeled probes of 191 bp using the Genius System PCR DIG Probe Synthesis Kit (Boehringer-Mannheim Corporation, Indianapolis, Ind.) according to the manufacturer's instructions in a Stratagene Robocycler 40 (Stratagene, La Jolla, Calif.) programmed for 1 cycle at 95° C. for 2 minutes, 25 cycles each at 95° C. for 1 minute, 56° C. for 1 minute, and 72° C. for 1 minute, and 1 cycle at 72° C. for 7 minutes.

```
550-71-2:  5'-cttttcgtccttgtccagc-3'    (SEQ ID NO:6)
550-79-1:  5'-gcgtcatatgcgtctcc-3'      (SEQ ID NO:7)
```

Example 10

Screening of Chromosomal Libraries

Figure 8:
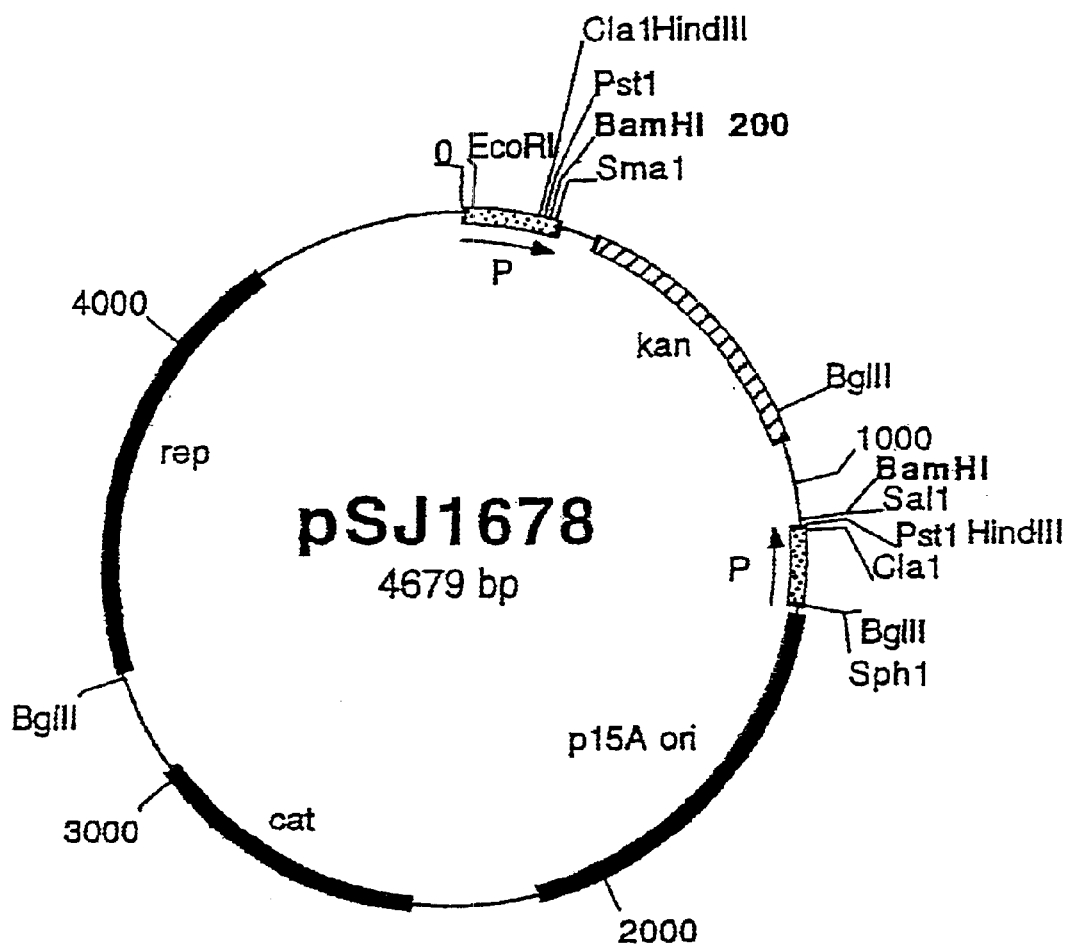
FIG. 8 shows a restriction map of pSJ1678.

Probe 191 bp described in Example 9 was used to screen a chromosomal library of *Sphingomonas capsulata* B46. The library was constructed by ligating Sau3A partially-digested (5–7 kb) *Sphingomonas capsulata* B46 chromosomal DNA into the BamHI sites of the vector pSJ1678 (FIG. 8). *Escherichia coli* XL1 Blue MR (Statagene, Inc., La Jolla, Calif.) was transformed with the chromosomal library and screened by colony lifts using the DIG-labeled 191 bp probe prepared with the Genius DIG Nonradioactive Nucleic Acid Labeling & Detection System (Boehringer Mannheim Biochemicals, Indianapolis, Ind.) according to the manufacturer's instructions. After screening approximately 5000 colonies, 5 colonies hybridized to the probe and the resulting plasmids were designated pMRT004.1-7, pMRT004.1-14, pMRT004.1-15, pMRT004.1-16 and pMRT004.1-17. Plasmid DNA from all positive clones were prepared using a QIAGEN Miniprep Plasmid Kit (Qiagen, Chatsworth, Calif.). Restriction analysis of plasmid DNA with restriction endonuclease PstI on a 1% agarose gel indicated that plasmid pMRT004.1-7 contained an insert of approximately 6 kb, plasmid pMRT004.1-14 contained an insert of approximately 5.6 kb, plasmid pMRT004.1-15 contained an insert of approximately 8.5 kb, plasmid pMRT004.1-16 contained an insert of approximately 8.6 kb and plasmid pMRT004.1-17 contained an insert of approximately 7.2 kb. This gel was further analysed by Southern hybridization with the Genius DIG Nonradioactive Nucleic Acid Labeling & Detection System according to the manufacturer's instructions using the DIG-labeled 191 bp probe. The results indicated that the DIG-labeled 191 bp probe hybridized to fragments that were approximately 3500 bp in pMRT004.1-7, pMRT004.1-14, pMRT004.1-16 and pMRT004.1-17, while it only hybridized to an approximate 1600 bp fragment in pMRT004.1-15.

Plasmid DNA from pMRT004.1-7 and pMRT004.1-14 were prepared using a QIAGEN Maxiprep Plasmid Kit (Qiagen, Chatsworth, Calif.). DNA from pMRT004.1-7 was then submitted for sequencing. DNA sequencing was performed with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.) according to the manufacturer's instructions. The results indicated that approximately one third of the aminopeptidase I gene, towards the N-terminus of the protein, was missing from this clone. Thus, the rest of the aminopeptidase I gene was obtained by sequencing clone pMRT004.1-14 which appeared to contain the entire aminopeptidase I gene based on restriction analysis with AvaI, SphI and EcoRI.

Example 11

Isolation of the *Sphingomonas capsulata* Aminopeptidase I Gene via PCR

PCR was used to isolate the *Sphingomonas capsulata* aminopeptidase I gene as a NruI/BglII fragment from clone pMRT004.1-14 described in Example 10. Amplification was performed with primers 591-35-1 and 591-36-1, described below. Amplification reactions were prepared in 50 µl volume with 50 pmol of primers 591-35-1 and 591-36-1, 10 ng of pMRT004.1-14 plasmid DNA as template, 1×PCR buffer (Perkin-Elmer, Foster City, Calif.), 200 µM each of dATP, dCTP, dGTP, and dTTP, 1 µl DMSO and 0.5 U of AmpliTaq Gold (Perkin-Elmer, Foster City, Calif.). Reactions were incubated in a Stratagene Robocycler 40 (Stratagene, La Jolla, Calif.) programmed for 1 cycle at 95° C. for 10 minutes, 30 cycles each at 95° C. for 1.5 minutes, 55° C. for 1.5 minutes, and 72° C. for 3 minutes, and 1 cycle at 72° C. for 7 minutes.

(SEQ ID NO:8)
591-35-1: 5'-cgaatcggccagatctccatcg-3'

(SEQ ID NO:9)
591-36-1: 5'-gatcctggcgcagctcgcgaaggcgcagg-3'

The amplification resulted in a 2100 bp PCR product. The 2100 bp product was cloned into pCR2.1/TOPO from the Invitrogen TOPO/TA Cloning Kit according to manufacturer's instructions and sequenced as previously described. This new clone was labeled pMRT010-4. Comparison of the deduced amino acid sequence from pMRT010-4 with the known amino acid sequence of the aminopeptidase I from pMRT004.1-14 indicated that they were identical. However, at the DNA level, pMRT010-4 contained a silent point mutation at amino acid position 170, changing the codon ggt which encodes for a glycine to a ggc which also encodes for a glycine.

The aminopeptidase I clone encoded an open reading frame of 2019 bp encoding a polypeptide of 673 amino acids. The nucleotide sequence (SEQ ID NO:1) and deduced amino acid sequence (SEQ ID NO:2) are shown in FIG. 9. Using the SignalP program (Nielsen et al., 1997, *Protein Engineering* 10: 1–6) with cutoff values for max. C, max. Y, max. S, and mean S of 0.42, 0.34, 0.95, and 0.55, respectively, a signal peptide of 32 residues was predicted, hence indicating a molecular weight of approximately 70,600 daltons for the secreted aminopeptidase I. Thus, the mature aminopeptidase I is composed of 641 amino acids.

A comparative alignment of aminopeptidase sequences was undertaken using the BLAST 2.0 protein database search program (Altschul et al., 1997, *Nucleic Acids Research* 25: 3389–3402) with the following arguments: blastall-p blastp-a 4-e 10-E 0-v 500-b 250-I [query file]-d prot_all, where -p refers to the program name, -a refers to the number of processors to use, -e refers to the expectation value, -E refers to the cost to extend a gap, -v refers to number of One-line descriptions, -b refers to the number of alignments to show, -I refers to the query file, and -d refers to the database used for the search.

The BLAST search revealed that the *Sphingomonas capsulata* aminopeptidase I shares regions of identity with a Hypothetical 67 kDa protein from Synechocystis sp. of 23% (Accession Number Q55449).

Example 12

Cloning of the *Sphingomonas capsulata* Aminopeptidase I Gene into Bacillus Expression Vector pPL2419CAsub2-P$_{ter}$/498

The strategy to express and secrete the aminopeptidase I in Bacillus subtiliswas to clone the region of the aminopeptidase gene that encodes for the mature region of the protein behind a strong promoter and a gram positive signal sequence, in frame, in a Bacillus integration vector. Plasmid pCAsub2-P$_{ter}$/498 was chosen for expression and secretion since it encodes a strong promoter, P$_{ter}$, and a gram positive signal sequence from the Bacillus protease PD498 (U.S. Pat. No. 5,621,089). This plasmid had been previously constructed by digesting plasmid p498-5 (U.S. Pat. No. 5,621,089) with SphI, and the 2500 bp fragment containing the P$_{ter}$/498 expression cassette was cloned into the SphI site of pIC20R (Marsh et al., 1984, *Gene* 32: 481-485) to generate pIC20R-P$_{ter}$/498. pIC20R-P$_{ter}$/498 was then digested with HindIII and BamHI and the 2500 bp fragment containing the P$_{ter}$/498 expression cassette was cloned into the HindIII/BamHI site of pSJ2882 (WO 98/22598) to generate pSJ2882-P$_{ter}$/498. pSJ2882-P$_{ter}$/498 was digested with HindIII, treated with Klenow fragment to create blunt ends, and then digested with BamHI. The 2500 bp fragment containing the P$_{ter}$/498 expression cassette was then cloned into the NotI (filled in with Klenow fragment)/Bam HI site of the integration vector pCAsub2 (WO 98/22598) to generate pCAsub2-P$_{ter}$/498.

Figure 10:
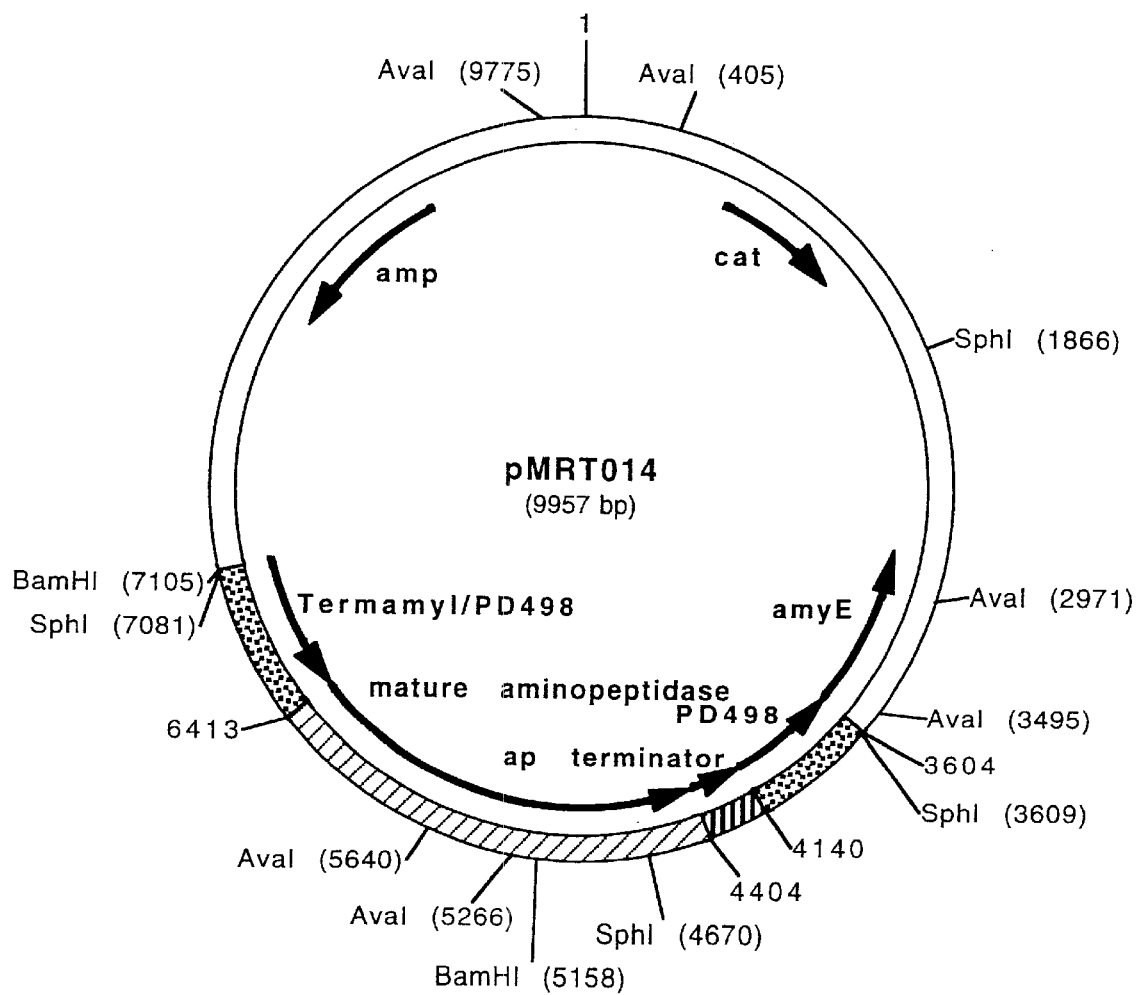
FIG. 10 shows a restriction map of pMRT014-1.

In order to make the final integration vector containing the aminopeptidase I gene, plasmid DNA from pCAsub2-P$_{ter}$/498 was digested with MscI and BglII, and plasmid DNA from pMRT010-4 was digested with NruI and BglII. The 8000 bp MscI/BglII fragment from pCAsub2-P$_{ter}$/498 and the 2100 bp NruI/BglII fragment from pMRT010-4 were isolated on 1% agarose gels and extracted with the QIAGEN Agarose DNA Gel Extraction Kit II (Qiagen, Inc., Chatsworth, Calif.) according to the manufacturer's instructions. Ligation of these two fragments was performed using the Rapid DNA Ligation Kit (Boehringer-Mannheim Corp., Indianapolis, Ind.) to generate the integration vector pMRT014-1 (FIG. 10) which was transformed directly into *Bacillus subtilis* PL1801 spoIIE cells according to the method of Petit et al., 1990, supra. Transformants were selected for chloramphenicol resistance. *Bacillus subtilis* PL1801 spoIIE is *Bacillus subtilis* 168 (Bacillus Stock Center, Columbus, Ohio) with deletions of the genes apr and npr and a Tn917 insertion into the spoIIE gene). Transformants were plated on Tryptone blood agar base (TBAB) plates containing chloramphenicol at 5 µg/ml, and incubated at 37° C., overnight. Genomic DNA from a transformant, designated *Bacillus subtilis* 1801IIe::pMRT014-1, was isolated using the Bacterial Isolation Protocol described in the Qiagen Genomic Handbook (Qiagen, Inc., Chatsworth, Calif.). Genomic DNA from *Bactillus subtilis* 1801IIe::pMRT014-1 was transformed into *Bacillus subtilis* 164Δ5 (WO 98/22598) as described above. A transformant designated *Bacillus subtilis* A164Δ5::pMRT014-1 was amplified three times on TBAB agar plates containing chloramphenicol at 30 µg/ml.

Example 13

Expression of *Sphingomonas capsulata* B46 Aminopeptidase I Gene in *Bacillus subtilis*

*Bacillus subtilis* A164Δ5::pMRT014-1 was cultivated in duplicate shake flasks at 37° C. and 250 rpm for 4 days containing 50 ml of PS-1 medium composed of 10% sucrose, 4% soybean flour, 0.42% anhydrous disodium phosphate, 0.01% pluronic acid, and 0.5% calcium carbonate. In addition, *Bacillus subtilis* A164Δ5::pCAsub2 containing the integration vector was used as a negative control.

Samples of 1 ml from each flask were removed at 24, 48 and 72 hours. The viability and stability of the aminopeptidase I integration was confirmed by plating on Luria-Bertani (LB) plates and subsequent patching on TBAB containing chloramphenicol at 30 µg/ml. In each instance, the integration was 100% stable as shown by the overnight growth of the patched colonies on the TBAB plates.

SDS-PAGE analysis using Novex 8–16% Tris-Glycine Precast Gels-1.0 mm×12 well and Novex DryEase Mini Gel Drying System (Novel Experimental Technology, San Diego, Calif.) was performed on 12 µl of supernatant from each flask, according to the manufacturer's instructions to determine the expression levels. Expression levels for the tested strain were also determined spectrophotometrically via aminopeptidase plate assays using L-Ala-pNA as substrate. SDS-PAGE gel data corroborated the spectrophotometric data in that aminopeptidase I expression was observed for *Bacillus subtilis* A164Δ5::pMRT014-1, with highest expression observed at 48 hours.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* XL1 Blue MR pMRT004.1-14 | NRRL B-30032 | Jun. 10, 1998 |

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid construct comprising a gene encoding a protein fused at the 5'-end of the coding region to the 3'-end of a nucleic acid sequence encoding a signal peptide consisting of the nucleotides 574 to 669 of SEQ ID NO: 1, wherein the gene is foreign to the nucleic acid sequence.

2. The nucleic acid construct of claim 1, wherein the nucleic acid sequence encoding a signal peptide consisting of nucleotides 574 to 669 of SEQ ID NO:1 is contained in plasmid pMRT004.1-14 which is contained in *E. coil* NRRL 8-30032.

3. The nucleic acid construct of claim 1, wherein the protein is a hormone, enzyme, receptor or portion thereof, antibody, or reporter.

4. The nucleic acid construct of claim 3, wherein the enzyme is an oxidoreductase, transferase, hydrolase, lyase, isomerase, or ligase.

5. A recombinant expression vector comprising the nucleic acid construct of claim 2.

6. A recombinant host cell comprising the nucleic acid construct of claim 2.

7. A method for producing a protein comprising (a) cultivating the recombinant host cell of claim 6 under conditions suitable for production of the protein; and (b) recovering the protein.

* * * * *